United States Patent
Morton et al.

(10) Patent No.: US 9,442,082 B2
(45) Date of Patent: Sep. 13, 2016

(54) X-RAY INSPECTION SYSTEM AND METHOD

(71) Applicant: Rapiscan Systems, Inc., Torrance, CA (US)

(72) Inventors: Edward James Morton, Guildford (GB); Francis Baldwin, Petersfield (GB)

(73) Assignee: Rapiscan Systems, Inc., Torrance, CA (US)

( * ) Notice: Subject to any disclaimer, the term of this patent is extended or adjusted under 35 U.S.C. 154(b) by 0 days.

(21) Appl. No.: 14/798,195

(22) Filed: Jul. 13, 2015

(65) Prior Publication Data

US 2016/0018342 A1    Jan. 21, 2016

Related U.S. Application Data

(60) Continuation of application No. 13/032,593, filed on Feb. 22, 2011, now Pat. No. 9,113,839, which is a continuation-in-part of application No. 12/835,682, filed on Jul. 13, 2010, now Pat. No. 8,204,173, and a (Continued)

(30) Foreign Application Priority Data

| Apr. 25, 2003 | (GB) | 0309371.3 |
| Apr. 25, 2003 | (GB) | 0309374.7 |
| Apr. 25, 2003 | (GB) | 0309379.6 |
| Apr. 25, 2003 | (GB) | 0309383.8 |
| Apr. 25, 2003 | (GB) | 0309385.3 |
| Apr. 25, 2003 | (GB) | 0309387.9 |
| Dec. 16, 2005 | (GB) | 0525593.0 |
| Feb. 25, 2009 | (GB) | 0903198.0 |

(51) Int. Cl.
*A61B 6/00* (2006.01)
*G01N 23/10* (2006.01)
(Continued)

(52) U.S. Cl.
CPC ............... *G01N 23/10* (2013.01); *A61B 6/032* (2013.01); *A61B 6/4028* (2013.01);
(Continued)

(58) Field of Classification Search
CPC .. A61B 6/4233; A61B 6/4241; A61B 6/482; G01N 23/087; G01T 1/2006; G01T 1/2008; G01T 1/24; G01T 1/362; G01T 1/366
See application file for complete search history.

(56) References Cited

U.S. PATENT DOCUMENTS

| 2,299,251 A | 10/1942 | Perbal |
| 2,831,123 A | 4/1958 | Daly |

(Continued)

FOREIGN PATENT DOCUMENTS

| AT | 392160 B | 2/1991 |
| AU | 2003254124 A1 | 2/2004 |

(Continued)

OTHER PUBLICATIONS

International Search Report, PCT/US2011/25777, Jul. 26, 2011, Rapiscan Systems, Inc.

(Continued)

*Primary Examiner* — Thomas R Artman
(74) *Attorney, Agent, or Firm* — Novel IP

(57) ABSTRACT

The present specification discloses an X-ray system for processing X-ray data to determine an identity of an object under inspection. The X-ray system includes an X-ray source for transmitting X-rays, where the X-rays have a range of energies, through the object, a detector array for detecting the transmitted X-rays, where each detector outputs a signal proportional to an amount of energy deposited at the detector by a detected X-ray, and at least one processor that reconstructs an image from the signal, where each pixel within the image represents an associated mass attenuation coefficient of the object under inspection at a specific point in space and for a specific energy level, fits each of pixel to a function to determine the mass attenuation coefficient of the object under inspection at the point in space; and uses the function to determine the identity of the object under inspection.

9 Claims, 8 Drawing Sheets

Related U.S. Application Data continuation-in-part of application No. 12/792,931, filed on Jun. 3, 2010, now Pat. No. 8,331,535, which is a continuation-in-part of application No. 12/788,083, filed on May 26, 2010, now Pat. No. 8,451,974, which is a continuation-in-part of application No. 12/787,930, filed on May 26, 2010, now Pat. No. 8,223,919, and a continuation-in-part of application No. 12/478,757, filed on Jun. 4, 2009, now Pat. No. 8,094,784, which is a continuation-in-part of application No. 12/364,067, filed on Feb. 2, 2009, now abandoned, which is a continuation of application No. 12/033,035, filed on Feb. 19, 2008, now Pat. No. 7,505,563, which is a continuation of application No. 10/554,569, filed as application No. PCT/GB2004/001732 on Apr. 23, 2004, now Pat. No. 7,349,525, said application No. 12/788,083 is a division of application No. 12/697,073, filed on Jan. 29, 2010, now Pat. No. 8,085,897, which is a continuation of application No. 10/554,570, filed as application No. PCT/GB2004/001747 on Apr. 23, 2004, now Pat. No. 7,684,538, said application No. 12/792,931 is a continuation-in-part of application No. 12/758,764, filed on Apr. 12, 2010, now Pat. No. 7,929,663, which is a continuation of application No. 12/211,219, filed on Sep. 16, 2008, now Pat. No. 7,724,868, which is a continuation of application No. 10/554,655, filed as application No. PCT/GB2004/001751 on Apr. 23, 2004, now Pat. No. 7,440,543, application No. 12/792,931, which is a continuation-in-part of application No. 12/142,005, filed on Jun. 19, 2008, now Pat. No. 8,135,110, which is a continuation of application No. 12/097,442, filed as application No. PCT/GB2006/004684 on Dec. 15, 2006, now Pat. No. 7,876,879, and application No. 12/835,682, which is a continuation-in-part of application No. 12/787,878, filed on May 26, 2010, now Pat. No. 8,804,899, and a continuation-in-part of application No. 12/758,764, and a continuation-in-part of application No. 12/712,476, filed on Feb. 25, 2010, now Pat. No. 8,243,876, and a continuation-in-part of application No. 12/651,479, filed on Jan. 3, 2010, now abandoned, which is a continuation of application No. 10/554,654, filed as application No. PCT/GB2004/001731 on Apr. 23, 2004, now Pat. No. 7,664,230, and application No. 12/712,476, which is a continuation-in-part of application No. 12/485,897, filed on Jun. 16, 2009, now abandoned, which is a continuation of application No. 10/554,656, filed as application No. PCT/GB2004/001729 on Apr. 23, 2004, and application No. 12/712,476, which is a continuation-in-part of application No. 12/371,853, filed on Feb. 16, 2009, now Pat. No. 7,903,789, which is a continuation of application No. 10/554,975, filed as application No. PCT/GB2004/001741 on Apr. 23, 2004, now Pat. No. 7,512,215, and application No. 12/712,476, which is a continuation-in-part of application No. 12/364,067, filed on Feb. 2, 2009, now abandoned, and a continuation-in-part of application No. 12/211,219, filed on Sep. 16, 2008, now Pat. No. 7,724,868, and a continuation-in-part of application No. 12/097,422, and a continuation-in-part of application No. 10/554,570, said application No. 13/032,593 is a continuation-in-part of application No. 12/485,900, filed on Jun. 16, 2009, now Pat. No. 7,949,101, which is a continuation-in-part of application No. 12/097,422.

(60) Provisional application No. 61/225,257, filed on Jul. 14, 2009, provisional application No. 61/183,591, filed on Jun. 3, 2009, provisional application No. 61/181,070, filed on May 26, 2009, provisional application No. 61/181,068, filed on May 26, 2009, provisional application No. 61/181,077, filed on May 26, 2009, provisional application No. 61/155,572, filed on Feb. 26, 2009.

(51) Int. Cl.
*G01N 23/087* (2006.01)
*A61B 6/03* (2006.01)
*G01N 23/04* (2006.01)
*G01T 1/29* (2006.01)
*G01V 5/00* (2006.01)
*G01N 23/083* (2006.01)
*G01T 1/20* (2006.01)

(52) U.S. Cl.
CPC .......... *A61B 6/4085* (2013.01); *A61B 6/4233* (2013.01); *A61B 6/4241* (2013.01); *A61B 6/4266* (2013.01); *A61B 6/463* (2013.01); *A61B 6/482* (2013.01); *A61B 6/542* (2013.01); *G01N 23/04* (2013.01); *G01N 23/083* (2013.01); *G01N 23/087* (2013.01); *G01T 1/2985* (2013.01); *G01V 5/0008* (2013.01); *A61B 6/4208* (2013.01); *A61B 6/5205* (2013.01); *G01N 2223/601* (2013.01); *G01N 2223/639* (2013.01); *G01T 1/2008* (2013.01)

(56) References Cited

U.S. PATENT DOCUMENTS

| | | |
|---|---|---|
| 2,952,790 A | 9/1960 | Steen |
| 2,999,935 A | 9/1961 | Foster |
| 3,239,706 A | 3/1966 | Farrell |
| 3,707,672 A | 12/1972 | Miller |
| 3,713,156 A | 1/1973 | Pothier |
| 3,766,387 A | 10/1973 | Heffan |
| 3,768,645 A | 10/1973 | Conway |
| 3,784,837 A | 1/1974 | Holmstrom |
| 3,848,130 A | 11/1974 | Macovski |
| 3,854,049 A | 12/1974 | Mistretta |
| RE28,544 E | 9/1975 | Stein |
| 3,965,358 A | 6/1976 | Macovski |
| 3,980,889 A | 9/1976 | Haas |
| 4,047,035 A | 9/1977 | Dennhoven |
| 4,057,725 A | 11/1977 | Wagner |
| 4,105,922 A | 8/1978 | Lambert |
| 4,122,783 A | 10/1978 | Pretini |
| 4,139,771 A | 2/1979 | Dennhoven |
| 4,158,770 A | 6/1979 | Davis |
| 4,210,811 A | 7/1980 | Dennhoven |
| 4,216,499 A | 8/1980 | Dennhoven |
| 4,228,353 A | 10/1980 | Johnson |
| 4,259,721 A | 3/1981 | Kuznia |
| 4,266,425 A | 5/1981 | Allport |
| 4,274,005 A | 6/1981 | Yamamura |
| 4,297,580 A | 10/1981 | Juner |
| 4,340,816 A | 7/1982 | Schott |
| 4,352,021 A | 9/1982 | Boyd |
| 4,366,382 A | 12/1982 | Kotowski |
| 4,375,695 A | 3/1983 | Harding |
| 4,384,209 A | 5/1983 | Wagner |
| 4,399,403 A | 8/1983 | Strandberg |
| 4,430,568 A | 2/1984 | Yoshida |
| 4,468,802 A | 8/1984 | Friedel |
| 4,471,343 A | 9/1984 | Lemelson |
| 4,566,113 A | 1/1986 | Doenges |
| 4,571,491 A | 2/1986 | Vinegar |
| 4,599,740 A | 7/1986 | Cable |
| 4,622,688 A | 11/1986 | Diemer |
| 4,641,330 A | 2/1987 | Herwig |
| 4,672,649 A | 6/1987 | Rutt |
| 4,675,890 A | 6/1987 | Plessis |

(56) References Cited

U.S. PATENT DOCUMENTS

| | | | |
|---|---|---|---|
| 4,736,401 A | 4/1988 | Donges |
| 4,754,469 A | 6/1988 | Harding |
| 4,788,704 A | 11/1988 | Donges |
| 4,788,706 A | 11/1988 | Jacobson |
| 4,789,930 A | 12/1988 | Sones |
| 4,825,454 A | 4/1989 | Annis |
| RE32,961 E | 6/1989 | Wagner |
| 4,866,745 A | 9/1989 | Akai |
| 4,868,856 A | 9/1989 | Frith |
| 4,884,289 A | 11/1989 | Glockmann |
| 4,887,604 A | 12/1989 | Shefer |
| 4,956,856 A | 9/1990 | Harding |
| 4,958,363 A | 9/1990 | Nelson |
| 4,975,968 A | 12/1990 | Yukl |
| 4,979,202 A | 12/1990 | Siczek |
| 4,987,584 A | 1/1991 | Doenges |
| 4,991,189 A | 2/1991 | Boomgaarden |
| 5,007,072 A | 4/1991 | Jenkins |
| 5,008,911 A | 4/1991 | Harding |
| 5,022,062 A | 6/1991 | Annis |
| 5,033,106 A | 7/1991 | Kita |
| 5,056,124 A | 10/1991 | Kakimoto |
| 5,065,418 A | 11/1991 | Bermbach |
| 5,081,456 A | 1/1992 | Michiguchi |
| 5,091,924 A | 2/1992 | Bermbach |
| 5,098,640 A | 3/1992 | Gozani |
| 5,105,452 A | 4/1992 | McInerney |
| 5,144,191 A | 9/1992 | Jones |
| 5,155,365 A | 10/1992 | Cann |
| 5,172,401 A | 12/1992 | Asari |
| 5,179,581 A | 1/1993 | Annis |
| 5,181,234 A | 1/1993 | Smith |
| 5,182,764 A | 1/1993 | Peschmann |
| 5,224,144 A | 6/1993 | Annis |
| 5,227,800 A | 7/1993 | Huguenin |
| 5,237,598 A | 8/1993 | Albert |
| 5,247,556 A | 9/1993 | Eckert |
| 5,247,561 A | 9/1993 | Kotowski |
| 5,253,283 A | 10/1993 | Annis |
| 5,259,014 A | 11/1993 | Brettschneider |
| 5,263,075 A | 11/1993 | McGann |
| 5,265,144 A | 11/1993 | Harding |
| 5,272,627 A | 12/1993 | Maschhoff |
| 5,313,511 A | 5/1994 | Annis |
| 5,319,547 A | 6/1994 | Krug |
| 5,339,080 A | 8/1994 | Steinway |
| 5,345,240 A | 9/1994 | Frazier |
| 5,365,567 A | 11/1994 | Ohtsuchi |
| 5,367,552 A | 11/1994 | Peschmann |
| 5,379,334 A | 1/1995 | Zimmer |
| 5,410,156 A | 4/1995 | Miller |
| 5,412,702 A | 5/1995 | Sata |
| 5,420,905 A | 5/1995 | Bertozzi |
| 5,467,377 A | 11/1995 | Dawson |
| 5,481,584 A | 1/1996 | Tang |
| 5,490,196 A | 2/1996 | Rudich |
| 5,490,218 A | 2/1996 | Krug |
| 5,493,596 A | 2/1996 | Annis |
| 5,511,104 A | 4/1996 | Mueller |
| 5,524,133 A | 6/1996 | Neale |
| 5,552,705 A | 9/1996 | Keller |
| 5,557,108 A | 9/1996 | Tumer |
| 5,557,283 A | 9/1996 | Sheen |
| 5,570,403 A * | 10/1996 | Yamazaki ............... A61B 6/032 378/19 |
| 5,600,303 A | 2/1997 | Husseiny |
| 5,600,700 A | 2/1997 | Krug |
| 5,604,778 A | 2/1997 | Polacin |
| 5,606,167 A | 2/1997 | Miller |
| 5,633,906 A | 5/1997 | Hell |
| 5,633,907 A | 5/1997 | Gravelle |
| 5,638,420 A | 6/1997 | Armistead |
| 5,642,393 A | 6/1997 | Krug |
| 5,642,394 A | 6/1997 | Rothschild |
| 5,648,997 A | 7/1997 | Chao |
| 5,651,047 A | 7/1997 | Moorman |
| 5,661,774 A | 8/1997 | Gordon |
| 5,666,393 A | 9/1997 | Annis |
| 5,687,210 A | 11/1997 | Maitrejean |
| 5,689,239 A | 11/1997 | Turner |
| 5,689,541 A | 11/1997 | Schardt |
| 5,692,028 A | 11/1997 | Geus |
| 5,712,926 A | 1/1998 | Eberhard |
| 5,745,543 A | 4/1998 | De |
| 5,751,837 A | 5/1998 | Watanabe |
| 5,764,683 A | 6/1998 | Swift |
| 5,768,334 A | 6/1998 | Maitrejean |
| 5,787,145 A | 7/1998 | Geus |
| 5,796,802 A | 8/1998 | Gordon |
| 5,805,660 A | 9/1998 | Perion |
| 5,812,630 A | 9/1998 | Blaffert |
| 5,818,897 A | 10/1998 | Gordon |
| 5,838,758 A | 11/1998 | Krug |
| 5,838,759 A | 11/1998 | Armistead |
| 5,841,831 A | 11/1998 | Hell |
| 5,859,891 A | 1/1999 | Hibbard |
| 5,864,146 A * | 1/1999 | Karellas ............... A61B 6/4258 250/581 |
| 5,881,122 A | 3/1999 | Crawford |
| 5,887,047 A | 3/1999 | Bailey |
| 5,901,198 A | 5/1999 | Crawford |
| 5,903,623 A | 5/1999 | Swift |
| 5,905,806 A | 5/1999 | Eberhard |
| 5,909,477 A | 6/1999 | Crawford |
| 5,910,973 A | 6/1999 | Grodzins |
| 5,930,326 A | 7/1999 | Rothschild |
| 5,940,468 A | 8/1999 | Huang |
| 5,943,388 A | 8/1999 | Tuemer |
| 5,966,422 A | 10/1999 | Dafni |
| 5,974,111 A | 10/1999 | Krug |
| 5,982,843 A | 11/1999 | Bailey |
| 5,987,097 A | 11/1999 | Salasoo |
| 6,018,562 A | 1/2000 | Willson |
| 6,021,174 A | 2/2000 | Campbell |
| 6,026,135 A | 2/2000 | McFee |
| 6,026,143 A | 2/2000 | Simanovsky |
| 6,026,171 A | 2/2000 | Hiraoglu |
| 6,031,890 A | 2/2000 | Bermbach |
| 6,035,014 A | 3/2000 | Hiraoglu |
| 6,037,597 A | 3/2000 | Karavolos |
| 6,054,712 A | 4/2000 | Komardin |
| 6,058,158 A | 5/2000 | Eiler |
| 6,067,344 A | 5/2000 | Grodzins |
| 6,067,366 A | 5/2000 | Simanovsky |
| 6,075,871 A | 6/2000 | Simanovsky |
| 6,076,400 A | 6/2000 | Bechwati |
| 6,078,642 A | 6/2000 | Simanovsky |
| 6,081,580 A | 6/2000 | Grodzins |
| 6,088,423 A | 7/2000 | Krug |
| 6,091,795 A | 7/2000 | Schafer |
| 6,094,472 A | 7/2000 | Smith |
| 6,108,396 A | 8/2000 | Bechwati |
| 6,111,974 A | 8/2000 | Hiraoglu |
| 6,118,850 A | 9/2000 | Mayo |
| 6,118,852 A | 9/2000 | Rogers |
| 6,122,343 A | 9/2000 | Pidcock |
| 6,125,167 A | 9/2000 | Morgan |
| 6,128,365 A | 10/2000 | Bechwati |
| 6,149,592 A | 11/2000 | Yanof |
| 6,151,381 A | 11/2000 | Grodzins |
| 6,163,591 A | 12/2000 | Benjamin |
| 6,181,765 B1 | 1/2001 | Sribar |
| 6,183,139 B1 | 2/2001 | Solomon |
| 6,184,841 B1 | 2/2001 | Shober |
| 6,185,272 B1 | 2/2001 | Hiraoglu |
| 6,188,743 B1 | 2/2001 | Tybinkowski |
| 6,188,745 B1 | 2/2001 | Gordon |
| 6,188,747 B1 | 2/2001 | Geus |
| 6,192,101 B1 | 2/2001 | Grodzins |
| 6,192,104 B1 | 2/2001 | Adams |
| 6,195,413 B1 | 2/2001 | Geus |
| 6,195,444 B1 | 2/2001 | Simanovsky |
| 6,198,795 B1 | 3/2001 | Naumann |
| 6,216,540 B1 | 4/2001 | Nelson |

(56) References Cited

U.S. PATENT DOCUMENTS

| | | | |
|---|---|---|---|
| 6,218,943 B1 | 4/2001 | Ellenbogen | |
| 6,236,709 B1 | 5/2001 | Perry | |
| 6,249,567 B1 | 6/2001 | Rothschild | |
| 6,252,929 B1 | 6/2001 | Swift | |
| 6,252,932 B1 | 6/2001 | Arakawa | |
| 6,256,369 B1 | 7/2001 | Lai | |
| 6,256,404 B1 | 7/2001 | Gordon | |
| 6,269,142 B1 | 7/2001 | Smith | |
| 6,272,230 B1 | 8/2001 | Hiraoglu | |
| 6,278,115 B1 | 8/2001 | Annis | |
| 6,282,260 B1 | 8/2001 | Grodzins | |
| 6,288,676 B1 | 9/2001 | Maloney | |
| 6,292,533 B1 | 9/2001 | Swift | |
| 6,301,326 B2 | 10/2001 | Bjorkholm | |
| 6,304,629 B1 | 10/2001 | Conway | |
| 6,317,509 B1 | 11/2001 | Simanovsky | |
| 6,320,933 B1 | 11/2001 | Grodzins | |
| 6,324,249 B1 | 11/2001 | Fazzio | |
| 6,332,015 B1 * | 12/2001 | Honda | A61B 6/4233 378/98.11 |
| 6,342,696 B1 | 1/2002 | Chadwick | |
| 6,345,113 B1 | 2/2002 | Crawford | |
| 6,347,132 B1 | 2/2002 | Annis | |
| 6,356,620 B1 | 3/2002 | Rothschild | |
| 6,359,582 B1 | 3/2002 | MacAleese | |
| 6,417,797 B1 | 7/2002 | Cousins | |
| 6,418,189 B1 | 7/2002 | Schafer | |
| 6,424,695 B1 | 7/2002 | Grodzins | |
| 6,429,578 B1 | 8/2002 | Danielsson | |
| 6,430,255 B2 | 8/2002 | Fenkart | |
| 6,434,219 B1 | 8/2002 | Rothschild | |
| 6,435,715 B1 | 8/2002 | Betz | |
| 6,438,201 B1 * | 8/2002 | Mazess | A61B 6/405 378/108 |
| 6,442,233 B1 | 8/2002 | Grodzins | |
| 6,445,765 B1 | 9/2002 | Frank | |
| 6,453,003 B1 | 9/2002 | Springer | |
| 6,453,007 B2 | 9/2002 | Adams | |
| 6,456,093 B1 | 9/2002 | Merkel | |
| 6,456,684 B1 | 9/2002 | Mun | |
| 6,459,755 B1 | 10/2002 | Li | |
| 6,459,761 B1 | 10/2002 | Grodzins et al. | |
| 6,459,764 B1 | 10/2002 | Grodzins | |
| 6,469,624 B1 | 10/2002 | Whan | |
| 6,473,487 B1 | 10/2002 | Le | |
| RE37,899 E | 11/2002 | Grodzins | |
| 6,480,141 B1 | 11/2002 | Toth | |
| 6,483,894 B2 | 11/2002 | Hartick | |
| 6,501,414 B2 | 12/2002 | Arndt | |
| 6,507,025 B1 | 1/2003 | Verbinski et al. | |
| 6,532,276 B1 | 3/2003 | Hartick | |
| 6,542,574 B2 | 4/2003 | Grodzins | |
| 6,542,578 B2 | 4/2003 | Ries | |
| 6,542,580 B1 | 4/2003 | Carver | |
| 6,546,072 B1 | 4/2003 | Chalmers | |
| 6,552,346 B2 | 4/2003 | Verbinski | |
| 6,556,653 B2 | 4/2003 | Hussein | |
| 6,563,903 B2 | 5/2003 | Kang | |
| 6,563,906 B2 | 5/2003 | Hussein | |
| 6,580,778 B2 | 6/2003 | Meder | |
| 6,584,170 B2 | 6/2003 | Aust | |
| 6,590,956 B2 | 7/2003 | Fenkart et al. | |
| 6,597,760 B2 | 7/2003 | Beneke | |
| 6,606,516 B2 | 8/2003 | Levine | |
| 6,618,466 B1 | 9/2003 | Ning | |
| 6,628,745 B1 | 9/2003 | Annis | |
| 6,636,581 B2 | 10/2003 | Sorenson | |
| 6,647,091 B2 | 11/2003 | Fenkart et al. | |
| 6,647,094 B2 | 11/2003 | Harding et al. | |
| 6,647,095 B2 | 11/2003 | Hsieh | |
| 6,650,276 B2 | 11/2003 | Lawless | |
| 6,653,588 B1 | 11/2003 | Gillard-Hickman | |
| 6,658,087 B2 | 12/2003 | Chalmers | |
| 6,661,866 B1 | 12/2003 | Limkeman | |
| 6,663,280 B2 | 12/2003 | Doenges | |
| 6,665,373 B1 | 12/2003 | Kotowski | |
| 6,665,433 B2 | 12/2003 | Roder | |
| 6,687,333 B2 | 2/2004 | Carroll et al. | |
| 6,690,766 B2 | 2/2004 | Kresse | |
| 6,707,879 B2 | 3/2004 | McClelland et al. | |
| 6,715,533 B2 | 4/2004 | Kresse | |
| 6,721,387 B1 | 4/2004 | Naidu et al. | |
| 6,735,271 B1 | 5/2004 | Rand et al. | |
| 6,737,652 B2 | 5/2004 | Lanza et al. | |
| 6,748,043 B1 | 6/2004 | Dobbs | |
| 6,754,298 B2 | 6/2004 | Fessler | |
| 6,763,635 B1 | 7/2004 | Lowman | |
| 6,768,317 B2 | 7/2004 | Meoller | |
| 6,770,884 B2 | 8/2004 | Bryman | |
| 6,775,348 B2 | 8/2004 | Hoffman | |
| 6,785,357 B2 | 8/2004 | Bernardi | |
| 6,785,359 B2 | 8/2004 | Lemaitre | |
| 6,788,761 B2 | 9/2004 | Bijjani et al. | |
| 6,798,863 B2 | 9/2004 | Sato | |
| 6,807,248 B2 | 10/2004 | Mihara | |
| 6,812,426 B1 | 11/2004 | Kotowski | |
| 6,813,374 B1 | 11/2004 | Karimi et al. | |
| 6,816,571 B2 | 11/2004 | Bijjani et al. | |
| 6,827,265 B2 | 12/2004 | Knowles et al. | |
| 6,830,185 B2 | 12/2004 | Knowles | |
| 6,831,590 B1 | 12/2004 | Steinway | |
| 6,837,422 B1 | 1/2005 | Meder | |
| 6,837,432 B2 | 1/2005 | Tsikos | |
| 6,839,403 B1 | 1/2005 | Kotowski et al. | |
| 6,843,599 B2 | 1/2005 | Le | |
| 6,856,271 B1 | 2/2005 | Hausner | |
| 6,856,667 B2 | 2/2005 | Ellengogen | |
| 6,859,514 B2 | 2/2005 | Hoffman | |
| 6,876,322 B2 | 4/2005 | Keller | |
| 6,891,381 B2 | 5/2005 | Bailey | |
| 6,894,636 B2 | 5/2005 | Anderton | |
| 6,901,135 B2 | 5/2005 | Fox et al. | |
| 6,906,329 B2 | 6/2005 | Bryman | |
| 6,907,101 B2 | 6/2005 | Hoffman | |
| 6,920,196 B2 | 7/2005 | Ueno | |
| 6,920,197 B2 | 7/2005 | Kang | |
| 6,922,455 B2 | 7/2005 | Jurczyk et al. | |
| 6,922,460 B2 | 7/2005 | Skatter et al. | |
| 6,922,461 B2 | 7/2005 | Kang et al. | |
| 6,928,141 B2 | 8/2005 | Carver | |
| 6,933,504 B2 | 8/2005 | Hoffman et al. | |
| 6,934,354 B2 | 8/2005 | Hoffman | |
| 6,940,071 B2 | 9/2005 | Ramsden et al. | |
| 6,944,264 B2 | 9/2005 | Bijjani et al. | |
| 6,947,517 B2 | 9/2005 | Hoffman | |
| 6,950,492 B2 | 9/2005 | Besson | |
| 6,950,493 B2 | 9/2005 | Besson | |
| 6,952,163 B2 | 10/2005 | Huey et al. | |
| 6,953,935 B1 | 10/2005 | Hoffman | |
| 6,957,913 B2 | 10/2005 | Renkart et al. | |
| 6,962,289 B2 | 11/2005 | Vatan et al. | |
| 6,968,030 B2 | 11/2005 | Hoffman | |
| 6,968,034 B2 | 11/2005 | Ellengogen | |
| 6,971,577 B2 | 12/2005 | Tsikos et al. | |
| 6,973,158 B2 | 12/2005 | Besson | |
| 6,975,698 B2 | 12/2005 | Katcha et al. | |
| 6,978,936 B2 | 12/2005 | Tsikos et al. | |
| 6,980,627 B2 | 12/2005 | Qiu et al. | |
| 6,990,171 B2 | 1/2006 | Toth et al. | |
| 6,990,172 B2 | 1/2006 | Toth | |
| 6,991,371 B2 | 1/2006 | Georgeson et al. | |
| 6,993,115 B2 | 1/2006 | McGuire et al. | |
| 6,996,209 B2 | 2/2006 | Marek | |
| 7,010,083 B2 | 3/2006 | Hoffman | |
| 7,012,256 B1 | 3/2006 | Roos | |
| 7,012,989 B2 | 3/2006 | Holland | |
| 7,016,459 B2 | 3/2006 | Ellenbogen et al. | |
| 7,020,241 B2 | 3/2006 | Beneke et al. | |
| 7,020,242 B2 | 3/2006 | Ellenbogen | |
| 7,023,950 B1 | 4/2006 | Annis | |
| 7,023,956 B2 | 4/2006 | Heaton et al. | |
| 7,023,957 B2 | 4/2006 | Bijjani et al. | |
| 7,027,553 B2 | 4/2006 | Dunham et al. | |
| 7,027,554 B2 | 4/2006 | Gaultier et al. | |

(56) References Cited

U.S. PATENT DOCUMENTS

| | | |
|---|---|---|
| 7,031,430 B2 | 4/2006 | Kaucic, Jr. et al. |
| 7,031,434 B1 | 4/2006 | Saunders et al. |
| 7,034,313 B2 | 4/2006 | Hoffman |
| 7,039,154 B1 | 5/2006 | Ellenbogen et al. |
| 7,039,159 B2 | 5/2006 | Muenchau |
| 7,045,787 B1 | 5/2006 | Verbinski et al. |
| 7,046,756 B2 | 5/2006 | Hoffman |
| 7,046,761 B2 | 5/2006 | Ellenbogen et al. |
| 7,050,529 B2 | 5/2006 | Hoffman |
| 7,050,536 B1 | 5/2006 | Fenkart et al. |
| 7,050,540 B2 | 5/2006 | Wilkins |
| 7,054,408 B2 | 5/2006 | Jiang et al. |
| 7,062,009 B2 | 6/2006 | Karimi et al. |
| 7,062,011 B1 | 6/2006 | Tybinkowski et al. |
| 7,062,074 B1 | 6/2006 | Beneke |
| 7,064,334 B2 | 6/2006 | Hoffman et al. |
| 7,065,175 B2 | 6/2006 | Green |
| 7,065,179 B2 | 6/2006 | Block et al. |
| 7,068,750 B2 | 6/2006 | Toth et al. |
| 7,068,751 B2 | 6/2006 | Toth et al. |
| 7,072,434 B1 | 7/2006 | Tybinkowski et al. |
| 7,076,029 B2 | 7/2006 | Toth et al. |
| 7,078,699 B2 | 7/2006 | Seppi |
| 7,081,628 B2 | 7/2006 | Granfors et al. |
| 7,084,404 B2 | 8/2006 | Hoffman et al. |
| 7,087,902 B2 | 8/2006 | Wang et al. |
| 7,088,799 B2 | 8/2006 | Hoffman |
| 7,090,133 B2 | 8/2006 | Zhu |
| 7,092,481 B2 | 8/2006 | Hoffman |
| 7,092,485 B2 | 8/2006 | Kravis |
| 7,103,137 B2 | 9/2006 | Seppi et al. |
| 7,110,488 B2 | 9/2006 | Katcha et al. |
| 7,112,797 B2 | 9/2006 | Hoge |
| 7,116,749 B2 | 10/2006 | Besson |
| 7,116,751 B2 | 10/2006 | Ellenbogen et al. |
| 7,119,553 B2 | 10/2006 | Yang et al. |
| 7,120,222 B2 | 10/2006 | Hoffman |
| 7,123,681 B2 | 10/2006 | Ellenbogen et al. |
| 7,127,027 B2 | 10/2006 | Hoffman |
| 7,130,374 B1 | 10/2006 | Jacobs et al. |
| 7,133,491 B2 | 11/2006 | Bernardi et al. |
| 7,136,450 B2 | 11/2006 | Ying et al. |
| 7,136,451 B2 | 11/2006 | Ying |
| 7,139,367 B1 | 11/2006 | Le |
| 7,139,406 B2 | 11/2006 | McClelland et al. |
| 7,149,278 B2 | 12/2006 | Arenson et al. |
| 7,149,339 B2 | 12/2006 | Veneruso |
| 7,155,812 B1 | 1/2007 | Peterson et al. |
| 7,158,611 B2 | 1/2007 | Heismann et al. |
| 7,164,747 B2 | 1/2007 | Ellenbogen et al. |
| 7,164,750 B2 | 1/2007 | Nabors et al. |
| 7,166,458 B2 | 1/2007 | Ballerstadt et al. |
| 7,167,539 B1 | 1/2007 | Hoffman |
| 7,173,998 B2 | 2/2007 | Hoffman |
| 7,177,387 B2 | 2/2007 | Yasunaga et al. |
| 7,177,391 B2 | 2/2007 | Chapin et al. |
| 7,183,906 B2 | 2/2007 | Zanovitch |
| 7,187,756 B2 | 3/2007 | Gohno |
| 7,190,757 B2 | 3/2007 | Ying et al. |
| 7,197,113 B1 | 3/2007 | Katcha et al. |
| 7,197,116 B2 | 3/2007 | Dunham |
| 7,197,172 B1 | 3/2007 | Naidu et al. |
| 7,203,269 B2 | 4/2007 | Huber |
| 7,203,271 B2 | 4/2007 | Benz |
| 7,206,379 B2 | 4/2007 | Lemaitre |
| 7,207,713 B2 | 4/2007 | Lowman |
| 7,215,731 B1 | 5/2007 | Basu et al. |
| 7,215,738 B2 | 5/2007 | Muenchau et al. |
| 7,218,704 B1 | 5/2007 | Adams |
| 7,224,765 B2 | 5/2007 | Ellenbogen |
| 7,224,766 B2 | 5/2007 | Jiang et al. |
| 7,224,769 B2 | 5/2007 | Turner |
| 7,233,640 B2 | 6/2007 | Ikhlef et al. |
| 7,233,644 B1 | 6/2007 | Bendahan |
| 7,236,564 B2 | 6/2007 | Hopkins et al. |
| 7,238,945 B2 | 7/2007 | Hoffman et al. |
| 7,247,856 B2 | 7/2007 | Hoge |
| 7,251,310 B2 | 7/2007 | Smith |
| 7,260,170 B2 | 8/2007 | Arenson et al. |
| 7,260,171 B1 | 8/2007 | Arenson et al. |
| 7,260,172 B2 | 8/2007 | Arenson et al. |
| 7,260,173 B2 | 8/2007 | Wakayama et al. |
| 7,260,174 B2 | 8/2007 | Hoffman et al. |
| 7,260,182 B2 | 8/2007 | Toth et al. |
| 7,263,160 B2 | 8/2007 | Schlomka et al. |
| 7,266,180 B1 | 9/2007 | Saunders et al. |
| 7,272,429 B2 | 9/2007 | Walker et al. |
| 7,274,767 B2 | 9/2007 | Clayton et al. |
| 7,277,577 B2 | 10/2007 | Ying et al. |
| 7,279,120 B2 | 10/2007 | Cheng et al. |
| 7,280,631 B2 | 10/2007 | De Man et al. |
| 7,282,727 B2 | 10/2007 | Retsky |
| 7,283,604 B2 | 10/2007 | De Man et al. |
| 7,283,609 B2 | 10/2007 | Possin et al. |
| 7,295,019 B2 | 11/2007 | Yang et al. |
| 7,295,651 B2 | 11/2007 | Delgado et al. |
| 7,298,812 B2 | 11/2007 | Tkaczyk et al. |
| 7,302,083 B2 | 11/2007 | Larson et al. |
| 7,308,073 B2 | 12/2007 | Tkaczyk et al. |
| 7,308,074 B2 | 12/2007 | Jiang et al. |
| 7,308,077 B2 | 12/2007 | Bijjani et al. |
| 7,317,195 B2 | 1/2008 | Eikman |
| 7,317,390 B2 | 1/2008 | Huey et al. |
| 7,319,737 B2 | 1/2008 | Singh |
| 7,322,745 B2 | 1/2008 | Agrawal |
| 7,324,625 B2 | 1/2008 | Eilbert |
| 7,327,853 B2 | 2/2008 | Ying et al. |
| 7,330,527 B2 | 2/2008 | Hoffman et al. |
| 7,330,535 B2 | 2/2008 | Arenson et al. |
| 7,333,587 B2 | 2/2008 | De |
| 7,333,588 B2 | 2/2008 | Mistretta et al. |
| 7,333,589 B2 | 2/2008 | Ellenbogen et al. |
| 7,335,887 B1 | 2/2008 | Verbinski et al. |
| 7,336,769 B2 | 2/2008 | Arenson et al. |
| 7,349,525 B2 | 3/2008 | Morton |
| 7,369,640 B2 | 5/2008 | Seppi |
| 7,369,643 B2 | 5/2008 | Kotowski |
| 7,372,934 B2 | 5/2008 | De |
| 7,400,701 B1 | 7/2008 | Cason |
| 7,412,026 B2 * | 8/2008 | Liu ..................... A61B 6/484 378/62 |
| 7,426,260 B2 * | 9/2008 | Cantu ................. G01T 1/295 250/370.11 |
| 7,440,543 B2 | 10/2008 | Morton |
| 7,486,760 B2 | 2/2009 | Harding |
| 7,486,769 B2 | 2/2009 | Brondo |
| 7,492,855 B2 | 2/2009 | Hopkins |
| 7,505,563 B2 | 3/2009 | Morton |
| 7,564,939 B2 | 7/2009 | Morton |
| 7,579,845 B2 | 8/2009 | Peschmann |
| 7,590,215 B2 | 9/2009 | Schlomka |
| 7,593,506 B2 | 9/2009 | Cason |
| 7,596,275 B1 | 9/2009 | Richardson |
| 7,636,638 B2 | 12/2009 | Russ |
| 7,643,866 B2 | 1/2010 | Heismann |
| 7,649,981 B2 | 1/2010 | Seppi |
| 7,664,230 B2 | 2/2010 | Morton |
| 7,684,538 B2 | 3/2010 | Morton |
| 7,724,868 B2 | 5/2010 | Morton |
| 7,734,066 B2 | 6/2010 | DeLia |
| 7,769,132 B1 | 8/2010 | Hurd |
| 7,778,382 B2 | 8/2010 | Hoffman |
| 7,835,495 B2 | 11/2010 | Harding |
| 7,876,879 B2 | 1/2011 | Morton |
| 7,885,372 B2 * | 2/2011 | Edic ................... A61B 6/032 378/158 |
| 7,903,789 B2 | 3/2011 | Morton |
| 7,929,663 B2 | 4/2011 | Morton |
| 7,949,101 B2 | 5/2011 | Morton |
| 7,970,096 B2 * | 6/2011 | Pavlovich ........... A61B 6/032 378/156 |
| 8,111,803 B2 * | 2/2012 | Edic ................... A61B 6/4035 378/146 |
| 8,135,110 B2 | 3/2012 | Morton |

(56) References Cited

U.S. PATENT DOCUMENTS

| | | | |
|---|---|---|---|
| 8,138,770 B2 | 3/2012 | Peschmann | |
| 8,243,876 B2 | 8/2012 | Morton | |
| 9,113,839 B2 * | 8/2015 | Morton | A61B 6/032 |
| 2001/0022346 A1 | 9/2001 | Katagami et al. | |
| 2001/0050972 A1 | 12/2001 | Yamada | |
| 2002/0008655 A1 | 1/2002 | Haj-Yousef | |
| 2002/0031202 A1 | 3/2002 | Callerame | |
| 2002/0094064 A1 | 7/2002 | Zhou | |
| 2002/0094117 A1 | 7/2002 | Funahashi | |
| 2002/0097836 A1 | 7/2002 | Grodzins | |
| 2002/0101958 A1 | 8/2002 | Bertsche | |
| 2002/0176531 A1 | 11/2002 | McClelland | |
| 2003/0009202 A1 | 1/2003 | Levine | |
| 2003/0021377 A1 | 1/2003 | Turner | |
| 2003/0048868 A1 | 3/2003 | Bailey | |
| 2003/0053597 A1 | 3/2003 | Flohr | |
| 2003/0076921 A1 | 4/2003 | Mihara | |
| 2003/0076924 A1 | 4/2003 | Mario | |
| 2003/0085163 A1 | 5/2003 | Chan | |
| 2003/0108155 A1 | 6/2003 | Wilkins | |
| 2003/0179126 A1 | 9/2003 | Jablonski | |
| 2003/0190011 A1 | 10/2003 | Beneke | |
| 2003/0216644 A1 | 11/2003 | Hall | |
| 2004/0017224 A1 | 1/2004 | Tumer | |
| 2004/0017888 A1 | 1/2004 | Seppi | |
| 2004/0077943 A1 | 4/2004 | Meaney | |
| 2004/0081270 A1 | 4/2004 | Heuscher | |
| 2004/0096030 A1 | 5/2004 | Banchieri | |
| 2004/0101098 A1 | 5/2004 | Bijjani | |
| 2004/0120456 A1 | 6/2004 | Ellenbogen | |
| 2004/0141584 A1 | 7/2004 | Bernardi | |
| 2004/0213378 A1 | 10/2004 | Zhou | |
| 2004/0223585 A1 | 11/2004 | Heismann | |
| 2004/0232054 A1 | 11/2004 | Brown | |
| 2004/0245449 A1 | 12/2004 | Nakashige | |
| 2004/0252807 A1 | 12/2004 | Skatter | |
| 2004/0258198 A1 | 12/2004 | Carver | |
| 2004/0258305 A1 | 12/2004 | Burnham | |
| 2005/0008073 A1 | 1/2005 | Techmer | |
| 2005/0031075 A1 | 2/2005 | Hopkins | |
| 2005/0053189 A1 | 3/2005 | Gohno | |
| 2005/0058242 A1 | 3/2005 | Peschmann | |
| 2005/0082491 A1 * | 4/2005 | Seppi | H01L 27/14676 250/370.11 |
| 2005/0084069 A1 | 4/2005 | Du | |
| 2005/0084073 A1 | 4/2005 | Seppi | |
| 2005/0089140 A1 | 4/2005 | Mario | |
| 2005/0105682 A1 | 5/2005 | Heumann | |
| 2005/0111610 A1 | 5/2005 | DeMan | |
| 2005/0111619 A1 | 5/2005 | Bijjani | |
| 2005/0156594 A1 | 7/2005 | Lorenz | |
| 2005/0157925 A1 | 7/2005 | Lorenz | |
| 2005/0169422 A1 | 8/2005 | Ellenbogen | |
| 2005/0169423 A1 | 8/2005 | Ellenbogen | |
| 2005/0180542 A1 | 8/2005 | Leue | |
| 2005/0190882 A1 | 9/2005 | McGuire | |
| 2005/0238232 A1 | 10/2005 | Ying | |
| 2005/0249416 A1 | 11/2005 | Leue | |
| 2005/0281390 A1 | 12/2005 | Johnson et al. | |
| 2006/0002585 A1 | 1/2006 | Larson | |
| 2006/0008047 A1 | 1/2006 | Zhou | |
| 2006/0018428 A1 | 1/2006 | Li et al. | |
| 2006/0109949 A1 | 5/2006 | Tkaczyk | |
| 2006/0113163 A1 | 6/2006 | Hu et al. | |
| 2006/0133571 A1 | 6/2006 | Winsor | |
| 2006/0134000 A1 | 6/2006 | Heismann | |
| 2006/0145771 A1 | 7/2006 | Strange | |
| 2006/0233295 A1 | 10/2006 | Edic | |
| 2006/0273259 A1 | 12/2006 | Li et al. | |
| 2006/0280286 A1 | 12/2006 | Kaval | |
| 2007/0003003 A1 | 1/2007 | Seppi et al. | |
| 2007/0025512 A1 | 2/2007 | Gertsenshteyn | |
| 2007/0053495 A1 | 3/2007 | Morton et al. | |
| 2007/0096030 A1 | 5/2007 | Li et al. | |
| 2007/0110215 A1 | 5/2007 | Hu et al. | |
| 2007/0122003 A1 | 5/2007 | Dobkin | |
| 2007/0133740 A1 | 6/2007 | Kang et al. | |
| 2007/0172024 A1 | 7/2007 | Morton et al. | |
| 2007/0183568 A1 | 8/2007 | Kang et al. | |
| 2007/0189597 A1 | 8/2007 | Limer | |
| 2007/0205367 A1 * | 9/2007 | Deman | G01T 1/2985 250/363.02 |
| 2007/0237288 A1 | 10/2007 | Tkaczyk | |
| 2007/0242802 A1 | 10/2007 | Dafni | |
| 2007/0263767 A1 | 11/2007 | Brondo | |
| 2008/0043912 A1 | 2/2008 | Harding | |
| 2008/0056432 A1 | 3/2008 | Pack | |
| 2008/0056435 A1 | 3/2008 | Basu et al. | |
| 2008/0198967 A1 | 8/2008 | Connelly | |
| 2008/0237480 A1 | 10/2008 | Robinson | |
| 2008/0267355 A1 | 10/2008 | Morton | |
| 2008/0304622 A1 | 12/2008 | Morton | |
| 2009/0003514 A1 | 1/2009 | Edic | |
| 2009/0010386 A1 | 1/2009 | Peschmann | |
| 2009/0034792 A1 | 2/2009 | Kennison | |
| 2009/0147910 A1 * | 6/2009 | Edic | A61B 6/032 378/5 |
| 2009/0161816 A1 | 6/2009 | DeMan | |
| 2009/0168958 A1 | 7/2009 | Cozzini | |
| 2009/0207967 A1 | 8/2009 | Liu | |
| 2009/0265386 A1 | 10/2009 | March | |
| 2010/0020920 A1 | 1/2010 | Mertelmeier | |
| 2010/0020934 A1 | 1/2010 | Morton | |
| 2010/0329532 A1 | 12/2010 | Masuda | |
| 2011/0243382 A1 * | 10/2011 | Morton | A61B 6/032 382/103 |
| 2011/0249788 A1 | 10/2011 | Nuesch | |

FOREIGN PATENT DOCUMENTS

| | | |
|---|---|---|
| CA | 2365045 | 6/2003 |
| CN | 85107860 A | 10/1986 |
| CN | 1050769 | 4/1991 |
| CN | 1130498 A | 9/1996 |
| CN | 1309768 | 8/2001 |
| CN | 1550215 A | 12/2004 |
| CN | 1626039 A | 6/2005 |
| CN | 1708256 A | 12/2005 |
| CN | 1795527 A | 6/2006 |
| CN | 100371689 C | 7/2006 |
| DE | 2729353 A1 | 1/1979 |
| DE | 4410757 A1 | 1/1995 |
| DE | 4436688 A1 | 4/1996 |
| DE | 102004056590 A1 | 6/2005 |
| EP | 0198276 A1 | 10/1986 |
| EP | 0424912 A2 | 5/1991 |
| EP | 0432568 | 6/1991 |
| EP | 0531993 A1 | 3/1993 |
| EP | 0564292 | 10/1993 |
| EP | 0584871 A1 | 3/1994 |
| EP | 0795919 A2 | 9/1997 |
| EP | 0873511 A1 | 10/1998 |
| EP | 0924742 A2 | 6/1999 |
| EP | 0930046 A2 | 7/1999 |
| EP | 1277439 A1 | 1/2003 |
| EP | 1298055 A2 | 4/2003 |
| EP | 1371970 A2 | 12/2003 |
| EP | 1374776 A1 | 1/2004 |
| EP | 1540318 A1 | 6/2005 |
| EP | 1558142 A1 | 8/2005 |
| EP | 1618584 A2 | 1/2006 |
| EP | 1689640 A2 | 8/2006 |
| EP | 1739413 | 5/2010 |
| EP | 2406809 | 1/2012 |
| FR | 2328280 A1 | 5/1977 |
| GB | 1497396 A | 1/1978 |
| GB | 1526041 A | 9/1978 |
| GB | 2015245 A | 9/1979 |
| GB | 2089109 A | 6/1982 |
| GB | 2133208 | 7/1984 |
| GB | 2212903 A | 8/1989 |
| GB | 2244900 | 12/1991 |
| GB | 2329817 A | 3/1995 |
| GB | 2285506 A | 7/1995 |

(56) References Cited

FOREIGN PATENT DOCUMENTS

| | | |
|---|---|---|
| GB | 2299251 | 9/1996 |
| GB | 2356453 A | 5/2001 |
| GB | 2414072 A | 11/2005 |
| GB | 2416655 A | 2/2006 |
| GB | 2416944 A | 2/2006 |
| GB | 2417821 A | 3/2006 |
| GB | 2418529 A | 3/2006 |
| GB | 2423687 A | 8/2006 |
| GB | 2437777 A | 11/2007 |
| GB | 2471421 A | 12/2010 |
| JP | 50012990 | 2/1975 |
| JP | S5427793 | 3/1979 |
| JP | 570175247 | 10/1982 |
| JP | 590016254 A | 1/1984 |
| JP | S5916254 A | 1/1984 |
| JP | 59075549 | 4/1984 |
| JP | 59174744 | 10/1984 |
| JP | 600015546 | 1/1985 |
| JP | S601554 A | 1/1985 |
| JP | S602144 | 1/1985 |
| JP | 600021440 | 2/1985 |
| JP | 60073442 A | 4/1985 |
| JP | S6104193 | 10/1986 |
| JP | 62064977 | 3/1987 |
| JP | S63150840 | 6/1988 |
| JP | 64034333 A | 2/1989 |
| JP | 05100037 A | 4/1993 |
| JP | 05192327 A | 8/1993 |
| JP | H05060381 | 9/1993 |
| JP | 5325851 | 12/1993 |
| JP | H05325851 | 12/1993 |
| JP | 060038957 | 2/1994 |
| JP | H06133960 | 5/1994 |
| JP | H06169911 | 6/1994 |
| JP | 6296607 | 10/1994 |
| JP | H08299322 | 11/1996 |
| JP | 10005206 A | 1/1998 |
| JP | 10075944 A | 3/1998 |
| JP | 1998075944 A | 3/1998 |
| JP | 10506195 | 6/1998 |
| JP | H10211196 A | 8/1998 |
| JP | 11146871 A | 6/1999 |
| JP | 11262486 A | 9/1999 |
| JP | 2000107173 A | 4/2000 |
| JP | 2001083171 | 3/2001 |
| JP | 2001176408 A | 6/2001 |
| JP | 2001233440 | 8/2001 |
| JP | 2001351551 | 12/2001 |
| JP | 2002503816 | 2/2002 |
| JP | 2002162472 | 6/2002 |
| JP | 2002168805 | 6/2002 |
| JP | 2002195961 | 7/2002 |
| JP | 2002257751 | 9/2002 |
| JP | 2002535625 | 10/2002 |
| JP | 2002320610 A | 11/2002 |
| JP | 2002370814 | 12/2002 |
| JP | 2003126075 A | 5/2003 |
| JP | 2003135442 | 5/2003 |
| JP | 2004000605 | 1/2004 |
| JP | 2004079128 A | 3/2004 |
| JP | 2004233206 | 8/2004 |
| JP | 2005013768 A | 1/2005 |
| JP | 2005110722 | 4/2005 |
| JP | 2005177469 A | 7/2005 |
| JP | 2005534009 | 11/2005 |
| JP | 2005534009 A | 11/2005 |
| JP | 2006071514 | 3/2006 |
| JP | 2006167463 | 6/2006 |
| JP | 2006320464 | 11/2006 |
| JP | 2006524809 A | 11/2006 |
| JP | 2007010455 | 1/2007 |
| JP | 2007500357 A | 1/2007 |
| JP | 2007508561 A | 4/2007 |
| JP | 2007533993 A | 11/2007 |
| JP | 2008113960 | 5/2008 |
| JP | 2008212840 | 9/2008 |
| JP | 2009083632 | 4/2009 |
| JP | 2009519457 | 5/2009 |
| NL | 1021026 | 1/2004 |
| NL | 1027596 C2 | 11/2005 |
| WO | 9217771 A1 | 10/1992 |
| WO | 9528715 A | 10/1995 |
| WO | 9718462 A1 | 5/1997 |
| WO | 9941676 | 8/1999 |
| WO | 9950882 | 10/1999 |
| WO | 9960387 A2 | 11/1999 |
| WO | 0231857 | 4/2002 |
| WO | 0231857 A1 | 4/2002 |
| WO | 03029844 | 4/2003 |
| WO | 03042674 | 5/2003 |
| WO | 03051201 | 6/2003 |
| WO | 03051201 A2 | 6/2003 |
| WO | 03065772 | 8/2003 |
| WO | 03088302 | 10/2003 |
| WO | 03105159 | 12/2003 |
| WO | 2004008968 A1 | 1/2004 |
| WO | 2004008970 A1 | 1/2004 |
| WO | 2004010127 A1 | 1/2004 |
| WO | 2004010381 A1 | 1/2004 |
| WO | 2004031755 | 4/2004 |
| WO | 2004037088 | 5/2004 |
| WO | 2004054329 A2 | 6/2004 |
| WO | 2004096050 | 11/2004 |
| WO | 2004097344 A2 | 11/2004 |
| WO | 2004097386 A1 | 11/2004 |
| WO | 2004097886 A2 | 11/2004 |
| WO | 2004097888 A2 | 11/2004 |
| WO | 2004097889 A2 | 11/2004 |
| WO | 2004105610 A | 12/2004 |
| WO | 2004111625 | 12/2004 |
| WO | 2005017566 A2 | 2/2005 |
| WO | 2005037074 | 4/2005 |
| WO | 2005050405 A2 | 6/2005 |
| WO | 2005084351 | 9/2005 |
| WO | 2005095931 | 10/2005 |
| WO | 2005102170 | 11/2005 |
| WO | 2006027122 A1 | 3/2006 |
| WO | 2006047718 | 5/2006 |
| WO | 2006135586 | 12/2006 |
| WO | 2006137919 | 12/2006 |
| WO | 2007051418 | 5/2007 |
| WO | 2007068933 A1 | 6/2007 |
| WO | 2007076707 | 7/2007 |
| WO | 2007079675 | 7/2007 |
| WO | 2008018021 | 2/2008 |
| WO | 2008027703 A2 | 3/2008 |
| WO | 2008094305 | 8/2008 |
| WO | 2008115275 | 9/2008 |
| WO | 2009005932 | 1/2009 |
| WO | 2009006044 | 1/2009 |
| WO | 2009024817 | 2/2009 |
| WO | 2009025935 | 2/2009 |
| WO | 2010097621 A2 | 9/2010 |
| WO | 2010138607 A1 | 12/2010 |
| WO | 2012115629 A1 | 8/2012 |

OTHER PUBLICATIONS

Notice of Allowance dated Apr. 17, 2015 for U.S. Appl. No. 13/032,593.
Chinese Patent Application No. 201110114529.2, Third Office Action, Issued on Jul. 14, 2014.
Rejection Decision for Chinese Patent Application No. 201110114529.2, dated Oct. 21, 2015.
Development of ultra-fast X-ray computed tomography scanner system, INS 98-43 6068772 A9823-8760J-016 (PHA); B9812-7510B-113 (EEA) NDN-174-0606-8771-7, Hori, K.; Fujimoto, T.; Kawanishi, K., Editor—Nalcioglu, O., Abbreviated Journal Title—1997 IEEE Nuclear Science Symposium, Conference Record (Cat No. 97CH36135), Part No. vol. 2, 1997, pp. 1003-1008 vol. 2, 2 vol. xlviii+1761 page(s), ISBN-0 7803 4258 5.
International Search Report, PCT/GB2004/001751, Mar. 21, 2005.
Great Britain Patent Application No. GB1017187.4, Combined Search and Examination Report, Jun. 21, 2007, CXR Limited.

(56) References Cited

OTHER PUBLICATIONS

International Search Report, PCT/GB2004/001729, Aug. 12, 2004, Rapiscan Systems, Inc.
International Search Report, PCT/GB2004/001747, Aug. 10, 2004.
International Search Report, PCT/GB2006/004684, May 23, 2007, CXR Ltd.
International Search Report, PCT/US2010/36221, Aug. 23, 2010, Rapiscan Security Productions, Inc.
Sheen, David et al. 'Three-Dimensional Millimeter-Wave Imaging for Concealed Weapon Detection', Sep. 2001, IEEE Transactions on Microwave Theory and Techniques, vol. 49, No. 9, pp. 1581-1592.
Appeal Decision, Japanese Patent Application No. 2009-274526, Dec. 3, 2015.
International Search Report, PCT/GB2004/001731, May 27, 2005.
International Search Report, PCT/GB2004/001732, Feb. 25, 2005.
International Search Report, PCT/GB2004/001741, Mar. 3, 2005.
Notice of Allowance dated Dec. 11, 2014 for U.S. Appl. No. 13/548,873.
Notice of Allowance dated Jan. 28, 2015 for U.S. Appl. No. 14/094,603.
Office Action for U.S. Appl. No. 12/485,900, Jul. 8, 2010.
Notice of Allowance for U.S. Appl. No. 12/485,900, Jan. 18, 2011.
Office Action for U.S. Appl. No. 13/086,708, Jun. 20, 2013.
Notice of Allowance for U.S. Appl. No. 13/086,708, Sep. 4, 2013.
Office Action for Japanese Application No. JP2011550657, dated Apr. 30, 2015.
Examination report for Application No. EP107132318, CXR limited, dated Feb. 23, 2015.
Examination Report for Application No. GB1114747.7 dated Jul. 30, 2014.
Letter to IPO for Application No. GB1114747.7 dated Dec. 2, 2014.
Second Examination Report for Application No. GB1114747.7 dated Mar. 6, 2015.
Third Examination Report for Application No. GB1114747.7 dated Jul. 28, 2015.
Fourth office action for Chinese Patent Application No. 2010800330571, Mar. 31, 2015.
Second office action for Japanese Application No. JP2011553531 mailed on Dec. 1, 2014.
Keevil, S.V., Lawinski, C.P. and Morton, E.J., 1987, "Measurement of the performance characteristics of anti-scatter grids.", Phys. Med. Biol., 32(3), 397-403.
Morton, E.J., Webb, S., Bateman, J.E., Clarke, L.J. and Shelton, C.G., 1990, "Three-dimensional x-ray micro-tomography for medical and biological applications.", Phys. Med. Biol., 35(7), 805-820.
Morton, E.J., Swindell, W., Lewis, D.G. and Evans, P.M., 1991, "A linear array scintillation-crystal photodiode detector for megavoltage imaging.", Med. Phys., 18(4), 681-691.
Morton, E.J., Lewis, D.G. and Swindell, W., 1988, "A method for the assessment of radiotherapy treatment precision", Brit. J. Radiol., Supplement 22, 25.
Swindell, W., Morton, E.J., Evans, P.M. and Lewis, D.G., 1991, "The design of megavoltage projection imaging systems: some theoretical aspects.", Med. Phys.,18(5), 855-866.
Morton, E.J., Evans, P.M., Ferraro, M., Young, E.F. and Swindell, W., 1991, "A video frame store facility for an external beam radiotherapy treatment simulator.", Brit. J. Radiol., 64, 747-750.
Antonuk, L.E., Yorkston, J., Kim, C.W., Huang, W., Morton, E.J., Longo, M.J. and Street, R.A., 1991, "Light response characteristics of amorphous silicon arrays for megavoltage and diagnostic imaging.", Mat. Res. Soc. Sym. Proc., 219, 531-536.
Yorkston, J., Antonuk, L.E., Morton, E.J., Boudry, J., Huang, W., Kim, C.W., Longo, M.J. and Street, R.A., 1991, "The dynamic response of hydrogenated amorphous silicon imaging pixels.", Mat. Res. Soc. Sym. Proc., 219, 173-178.
Evans, P.M., Gilderseve, J.Q., Morton, E.J., Swindell, W., Coles, R., Ferraro, M., Rawlings, C., Xiao, Z.R. and Dyer, J., 1992, "Image comparison techniques for use with megavoltage imaging systems.", Brit. J. Radiol., 65, 701-709.

Morton, E.J., Webb, S., Bateman, J.E., Clarke, L.J. and Shelton, C.G., 1989, "The development of 3D x-ray micro-tomography at sub 100 µm resolution with medical, industrial and biological applications.", Presentation at IEE colloquium "Medical scanning and imaging techniques of value in non-destructive testing", London, Nov. 3, 1989.
Antonuk, L.E., Boudry, J., Huang, W., McShan, D.L., Morton, E.J., Yorkston, J, Longo, M.J. and Street, R.A., 1992, "Demonstration of megavoltage and diagnostic x-ray imaging with hydrogenated amorphous silicon arrays.", Med. Phys., 19(6), 1455-1466.
Gildersleve, J.Q., Swindell, W. Evans, P.M., Morton, E.J., Rawlings, C. and Dearnaley, D.P., 1991, "Verification of patient positioning during radiotherapy using an integrated megavoltage imaging system.", in "Tumour Response Monitoring and Treatment Planning", Proceedings of the International Symposium of the W. Vaillant Foundation on Advanced Radiation Therapy, Munich, Germany, Ed A. Breit (Berlin: Springer), 693-695.
Lewis, D.G., Evans, P.M., Morton, E.J., Swindell, W. and Xiao, X.R., 1992, "A megavoltage CT scanner for radiotherapy verification.", Phys. Med. Biol., 37, 1985-1999.
Antonuk, L.E., Boudry, J., Kim, C.W., Longo, M.J., Morton, E.J., Yorkston, J. and Street, R.A., 1991, "Signal, noise and readout considerations in the development of amorphous silicon photodiode arrays for radiotherapy and diagnostic x-ray imaging.", SPIE vol. 1443 Medical Imaging V: Image Physics, 108-119.
Antonuk, L.E., Yorkston, J., Huang, W., Boudry, J., Morton, E.J., Longo, M.J. and Street, R.A., 1992, "Radiation response characteristics of amorphous silicon arrays for megavoltage radiotherapy imaging.", IEEE Trans. Nucl. Sci., 39,1069-1073.
Antonuk, L.E., Yorkston, J., Huang, W., Boudry, J., Morton, E.J., Longo, M.J. and Street, R.A., 1992, "Factors affecting image quality for megavoltage and diagnostic x-ray a-Si:H imaging arrays.", Mat. Res. Soc. Sym. Proc., 258, 1069-1074.
Antonuk, L.E., Boudry, J., Yorkston, J. Morton, E.J., Huang, W. and Street, R.A., 1992, "Development of thin-film, flat-panel arrays for diagnostic and radiotherapy imaging.", SPIE vol. 1651, Medical Imaging VI: Instrumentation, 94-105.
Yorkston, J., Antonuk, L.E., Seraji, N., Boudry, J., Huang, W., Morton, E.J., and Street, R.A., 1992, "Comparison of computer simulations with measurements from a-Si:H imaging arrays.", Mat. Res. Soc. Sym. Proc., 258, 1163-1168.
Morton, E.J., Antonuk, L.E., Berry, J.E., Boudry, J., Huang, W., Mody, P., Yorkston, J. and Longo, M.J., 1992, "A Camac based data acquisition system for flat-panel image array readout", Presentation at IEEE Nuclear Science Symposium, Orlando, Oct. 25-31, 1992.
Antonuk, L.E., Yorkston, J., Huang, W., Boudry, J. Morton, E.J. and Street, R.A., 1993, "Large area, flat-panel a-Si:H arrays for x-ray imaging.", SPIE vol. 1896, Medical Imaging 1993: Physics of Medical Imaging, 18-29.
Morton, E.J., Antonuk, L.E., Berry, J.E., Huang, W., Mody, P. and Yorkston, J., 1994, "A data acquisition system for flat-panel imaging arrays", IEEE Trans. Nucl. Sci., 41(4), 1150-1154.
Antonuk, L.E., Boudry, J., Huang, W., Lam, K.L., Morton, E.J., TenHaken, R.K., Yorkston, J. and Clinthorne, N.H., 1994, "Thin-film, flat-panel, composite imagers for projection and tomographic imaging", IEEE Trans. Med. Im., 13(3), 482-490.
Gildersleve, J., Dearnaley, D., Evans, P., Morton, E.J. and Swindell, W., 1994, "Preliminary clinical performance of a scanning detector for rapid portal imaging", Clin. Oncol., 6, 245-250.
Hess, R., De Antonis, P., Morton, E.J. and Gilboy, W.B., 1994, "Analysis of the pulse shapes obtained from single crystal CdZnTe radiation detectors", Nucl. Inst. Meth., A353, 76-79.
DeAntonis, P., Morton, E.J., T. Menezes, 1996, "Measuring the bulk resistivity of CdZnTe single crystal detectors using a contactless alternating electric field method", Nucl. Inst. Meth., A380, 157-159.
DeAntonis, P., Morton, E.J., Podd, F., 1996, "Infra-red microscopy of CdZnTe radiation detectors revealing their internal electric field structure under bias", IEEE Trans. Nucl. Sci., 43(3), 1487-1490.
Tavora, L.M.N., Morgado, R.E., Estep, R.J., Rawool-Sullivan, M., Gilboy, W.B. and Morton, E.J., 1998, "One-sided imaging of large, dense, objects using the 511 keV photons from induced pair production", IEEE Trans. Nucl. Sci., 45(3), 970-975.

(56) References Cited

OTHER PUBLICATIONS

Morton, E.J., 1995, "Archaeological potential of computerised tomography", Presentation at IEE Colloquium on "NDT in archaeology and art", London, May 25, 1995.

Tavora, L.M.N. and Morton, E.J., 1998, "Photon production using a low energy electron expansion of the EGS4 code system", Nucl. Inst. Meth., B143, 253-271.

Patel, D.C. and Morton, E.J., 1998, "Analysis of improved adiabatic pseudo-domino domino logic family", Electron. Lett., 34(19), 1829-1830.

Kundu, A and Morton, E.J., 1999, "Numerical simulation of argon-methane gas filled proportional counters", Nucl. Inst. Meth., A422, 286-290.

Luggar, R.D., Key, M.J., Morton, E.J. and Gilboy, W.B., 1999, "Energy dispersive X-ray scatter for measurement of oil/water ratios", Nucl. Inst. Meth., A422, 938-941.

Morton, E.J., Crockett, G.M., Sellin, P.J. and DeAntonis, P., 1999, "The charged particle response of CdZnTe radiation detectors", Nucl. Inst. Meth., A422, 169-172.

Morton, E.J., Clark, R.J. and Crowley, C., 1999, "Factors affecting the spectral resolution of scintillation detectors", Nucl. Inst. Meth., A422, 155-158.

Morton, E.J., Caunt, J.C., Schoop, K., Swinhoe, M., 1996, "A new handheld nuclear material analyser for safeguards purposes", Presentation at INMM annual meeting, Naples, Florida, Jul. 1996.

Hepworth, S., McJury, M., Oldham, M., Morton, E.J. and Doran, S.J., 1999, "Dose mapping of inhomogeneities positioned in radiosensitive polymer gels", Nucl. Inst. Meth., A422, 756-760.

Morton, E.J., Luggar, R.D., Key, M.J., Kundu, A., Tavora, L.M.N. and Gilboy, W.B., 1999, "Development of a high speed X-ray tomography system for multiphase flow imaging", IEEE Trans. Nucl. Sci., 46 III(1), 380-384.

Tavora, L.M.N., Morton, E.J., Santos, F.P. and Dias, T.H.V.T., 2000, "Simulation of X-ray tubes for imaging applications", IEEE Trans. Nucl. Sci., 47, 1493-1497.

Távora, L.M.N., Morton, E.J. and Gilboy, W.B., 2000, "Design considerations for transmission X-ray tubes operated at diagnostic energies", J. Phys. D: Applied Physics, 33(19), 2497-2507.

Morton, E.J., Hossain, M.A., DeAntonis, P. and Ede, A.M.D., 2001, "Investigation of Au-CdZnTe contacts using photovoltaic measurements", Nucl. Inst. Meth., A458, 558-562.

Ede, A.M.D., Morton, E.J. and DeAntonis, P., 2001, "Thin-film CdTe for imaging detector applications", Nucl. Inst. Meth., A458, 7-11.

Távora, L.M.N., Morton, E.J. and Gilboy, W.B., 2001, "Enhancing the ratio of fluorescence to bremsstrahlung radiation in X-ray tube spectra", App. Rad. and Isotopes, 54(1), 59-72.

Menezes, T. and Morton, E.J., 2001, "A preamplifier with digital output for semiconductor detectors", Nucl. Inst. Meth. A., A459, 303-318.

Johnson, D.R., Kyriou, J., Morton, E.J., Clifton, A.C. Fitzgerald, M. and MacSweeney, J.E., 2001, "Radiation protection in interventional radiology", Clin. Rad., 56(2), 99-106.

Tavora, L.M.N., Gilboy, W.B. and Morton, E.J., 2001, "Monte Carlo studies of a novel X-ray tube anode design", Rad. Phys. and Chem., 61, 527-529.

Morton, E.J., 1998, "Is film dead: the flat plate revolution", Keynote Talk, IPEM Annual Conference, Brighton, Sep. 14-17, 1998.

Luggar, R.D., Morton, E.J., Jenneson, P.M. and Key, M.J., 2001, "X-ray tomographic imaging in industrial process control", Rad. Phys. Chem., 61, 785-787.

Luggar, R.D., Morton, E.J., Key, M.J., Jenneson, P.M. and Gilboy, W.B., 1999, "An electronically gated multi-emitter X-ray source for high speed tomography", Presentation at SPIE Annual Meeting, Denver, Jul. 19-23, 1999.

Gregory, P.J., Hutchinson, D.J., Read, D.B., Jenneson, P.M., Gilboy, W.B. and Morton, E.J., 2001, "Non-invasive imaging of roots with high resolution X-ray microtomography", Plant and Soil, 255(1), 351-359.

Kundu, A., Morton, E.J., Key, M.J. and Luggar, R.D., 1999, "Monte Carlo simulations of microgap gas-filled proportional counters", Presentation at SPIE Annual Meeting, Denver, Jul. 19-23, 1999.

Hossain, M.A., Morton, E.J., and Ozsan, M.E., 2002, "Photo-electronic investigation of CdZnTe spectral detectors", IEEE Trans. Nucl. Sci, 49(4), 1960-1964.

Panman, A., Morton, E.J., Kundu, A and Sellin, P.J., 1999, "Optical Monte Carlo transport in scintillators", Presentation at SPIE Annual Meeting, Denver, Jul. 19-23, 1999.

Jenneson, P.M., Gilboy, W.B., Morton, E.J., and Gregory, P.J., 2003, "An X-ray micro-tomography system optimised for low dose study of living organisms", App. Rad. Isotopes, 58, 177-181.

Key, M.J., Morton, E.J., Luggar, R.D. and Kundu, A., 2003, "Gas microstrip detectors for X-ray tomographic flow imaging", Nucl. Inst. Meth., A496, 504-508.

Jenneson, P.M., Luggar, R.D., Morton, E.J., Gundogdu, O, and Tuzun, U, 2004, "Examining nanoparticle assemblies using high spatial resolution X-ray microtomography", J. App. Phys, 96(5), 2889-2894.

Tavora, L.M., Gilboy, W.B. and Morton, E.J., 2000, "Influence of backscattered electrons on X-ray tube output", Presentation and SPIE Annual Meeting, San Diego, Jul. 30-Aug. 3, 2000.

Wadeson, N., Morton, E.J., and Lionheart, W.B., 2010, "Scatter in an uncollimated x-ray CT machine based on a Geant4 Monte Carlo simulation", SPIE Medical Imaging 2010: Physics of Medical Imaging, Feb. 15-18, 2010, San Diego, USA.

Morton, E.J., 2010, "Position sensitive detectors in security: Users perspective", Invited talk, STFC meeting on position sensitive detectors, RAL, May 2010.

Office Action for Japanese Patent Application No. 2014-232429, dated Sep. 18, 2015.

US 5,987,079, 11/1999, Scott (withdrawn)

\* cited by examiner

X-RAY INSPECTION SYSTEM AND METHOD

CROSS-REFERENCE TO RELATED APPLICATIONS

The present specification is a continuation application of U.S. patent application Ser. No. 13/032,593, entitled "X-Ray Inspection System and Method" and filed on Feb. 2, 2011.

U.S. patent application Ser. No. 13/032,593 is a continuation-in-part application of U.S. patent application Ser. No. 12/835,682, entitled "System and Method for Image Reconstruction By Using Multi-Sheet Surface Rebinning", filed on Jul. 13, 2010, and issued on Jun. 19, 2012 as U.S. Pat. No. 8,204,173, which relies on U.S. Provisional Patent Application No. 61/225,257, entitled "Method for Image Reconstruction by Using Multi-Sheet Surface Rebinning" and filed on Jul. 14, 2009, for priority.

U.S. patent application Ser. No. 12/835,682 is also a continuation-in-part application of U.S. patent application Ser. No. 12/792,931, entitled "Graphite Backscattered Electron Shield for Use in an X-Ray Tube", filed on Jun. 3, 2010, and issued on Dec. 11, 2012 as U.S. Pat. No. 8,331,535, which relies on U.S. Provisional Patent Application No. 61/183,591, of the same title and filed on Jun. 3, 2009, for priority. U.S. patent application Ser. No. 12/835,682 is also a continuation-in-part application of U.S. patent application Ser. No. 12/788,083, entitled "X-Ray Tomographic Inspection System for the Identification of Specific Target Items", filed on May 26, 2010, and issued on May 28, 2013 as U.S. Pat. No. 8,451,974, which relies on U.S. Provisional Patent Application No. 61/181,070, of the same title and filed on May 26, 2009, for priority. U.S. patent application Ser. No. 12/835,682 is also a continuation-in-part application of U.S. patent application Ser. No. 12/787,930, of the same, filed on May 26, 2010, and issued on Jul. 17, 2012 as U.S. Pat. No. 8,223,919, which relies on U.S. Provisional Patent Application No. 61/181,068, of the same title and filed on May 26, 2009, for priority.

U.S. patent application Ser. No. 12/787,930 is also a continuation-in-part application of Ser. No. 12/478,757, entitled "X-Ray Sources", filed on Jun. 4, 2009, and issued on Jan. 10, 2012 as U.S. Pat. No. 8,094,784, which is a continuation-in-part application of U.S. patent application Ser. No. 12/364,067, entitled "X-Ray Sources" and filed on Feb. 2, 2009, which is a continuation application of U.S. patent application Ser. No. 12/033,035, of the same title, filed on Feb. 19, 2008, and issued on Mar. 17, 2009 as U.S. Pat. No. 7,505,563, which is a continuation application of U.S. patent application Ser. No. 10/554,569, of the same title, filed on Oct. 25, 2005, and issued on Mar. 25, 2008 as U.S. Pat. No. 7,349,525, which is a 371 national stage filing of PCT/GB2004/001732, of the same title and filed on Apr. 23, 2004, which, in turn, relies on Great Britain Patent Application Number 0309374.7, filed on Apr. 25, 2003, for priority.

U.S. patent application Ser. No. 12/788,083 is also a continuation-in-part application of U.S. patent application Ser. No. 12/697,073, entitled "X-Ray Scanning System", filed on Jan. 29, 2010, and issued on Dec. 27, 2011 as U.S. Pat. No. 8,085,897, which is a continuation application of U.S. patent application Ser. No. 10/554,570, entitled "X-Ray Scanning System", filed on Oct. 25, 2005, and issued on Mar. 23, 2010 as U.S. Pat. No. 7,684,538, which is a 371 national stage filing of PCT/GB2004/001747, of the same title and filed on Apr. 23, 2004, which, in turn, relies on Great Britain Patent Application Number 0309379.6, filed on Apr. 25, 2003, for priority.

U.S. patent application Ser. No. 12/792,931 is also a continuation-in-part application of U.S. patent application Ser. No. 12/758,764, entitled "X-Ray Monitoring", filed on Apr. 12, 2010, and issued on Apr. 19, 2011 as U.S. Pat. No. 7,929,663, which is a continuation application of U.S. patent application Ser. No. 12/211,219, of the same title, filed on Sep. 16, 2008, and issued on May 25, 2010 as U.S. Pat. No. 7,724,868, which is a continuation application of U.S. patent Ser. No. 10/554,655, of the same title, filed on Oct. 25, 2005, and issued on Oct. 21, 2008 as U.S. Pat. No. 7,440,543, which is a 371 national stage application of PCT/GB2004/001751, of the same title and filed on Apr. 23, 2004, which, in turn, relies on Great Britain Patent Application Number 0309385.3, filed on Apr. 25, 2003, for priority. U.S. patent application Ser. No. 12/792,931 is also a continuation-in-part application of U.S. patent application Ser. No. 12/142,005, entitled "X-Ray Tomography Inspection Systems", filed on Jun. 19, 2008, and issued on Mar. 13, 2012 as U.S. Pat. No. 8,135,110, which is a continuation application of U.S. patent application Ser. No. 12/097,422, of the same title, filed on Jun. 13, 2008, and issued on Jan. 25, 2011 as U.S. Pat. No. 7,876,879, which is a 371 national stage filing of PCT/GB2006/004684, of the same title and filed on Dec. 15, 2006, which, in turn, relies on Great Britain Patent Application Number 0525593.0, filed on Dec. 16, 2005, for priority.

U.S. patent application Ser. No. 12/835,682 is also a continuation-in-part application of U.S. patent application Ser. No. 12/787,878, entitled "Imaging, Data Acquisition, Data Transmission, and Data Distribution Methods and Systems for High Data Rate Tomographic X-Ray Scanners", filed on May 26, 2010, and issued on Aug. 12, 2014 as U.S. Pat. No. 8,804,899, which relies on U.S. Provisional Patent Application No. 61/181,077, of the same title and filed on May 26, 2009, for priority.

U.S. patent application Ser. No. 12/787,878 is also a continuation-in-part application of U.S. patent application Ser. No. 12/758,764, entitled "X-Ray Monitoring", filed on Apr. 12, 2010, and issued on Apr. 19, 2011 as U.S. Pat. No. 7,929,663.

U.S. patent application Ser. No. 12/787,878 is also a continuation-in-part application of U.S. patent application Ser. No. 12/712,476, entitled "X-Ray Scanners", filed on Feb. 25, 2010, and issued on Aug. 14, 2012 as U.S. Pat. No. 8,243,876, which relies on U.S. Provisional Patent Application No. 61/155,572, of the same title and filed on Feb. 26, 2009, and Great Britain Patent Application Number 0903198.0 filed on Feb. 25, 2009, for priority.

U.S. patent application Ser. No. 12/712,476 is also a continuation-in-part application of U.S. patent application Ser. No. 12/651,479, entitled "X-Ray Tubes" and filed on Jan. 3, 2010, which is a continuation application of U.S. patent application Ser. No. 10/554,654, filed on Oct. 25, 2005, and issued on Feb. 16, 2010 as U.S. Pat. No. 7,664,230, which is a 371 national stage application of PCT/GB2004/001731, of the same title and filed on Apr. 23, 2004, which, in turn, relies on Great Britain Patent Application Number 0309371.3, filed on Apr. 25, 2003, for priority.

U.S. patent application Ser. No. 12/712,476 is also a continuation-in-part application of U.S. patent application Ser. No. 12/485,897, entitled "Control Means for Heat Load in X-Ray Scanning Apparatus" and filed on Jun. 16, 2009, which is a continuation application of U.S. patent application Ser. No. 10/554,656, of the same title, filed on Oct. 25, 2005, and issued on Jul. 21, 2009 as U.S. Pat. No. 7,564,939, which is a 371 national stage application of PCT/GB2004/001729, of the same title and filed on Apr. 23, 2004, which, in turn, relies on Great Britain Application Number 0309387.9, filed on Apr. 25, 2003, for priority.

U.S. patent application Ser. No. 12/712,476 is also a continuation-in-part application of U.S. patent application Ser. No. 12/371,853, entitled "X-Ray Tube Electron Sources" and filed on Feb. 16, 2009, which is a continuation application of U.S. patent application Ser. No. 10/554,975, of the same title, filed on Oct. 25, 2005, and issued on Mar. 31, 2009 as U.S. Pat. No. 7,512,215, which is a 371 national stage application of PCT/GB2004/001741, of the same title and filed on Apr. 23, 2004 and which, in turn, relies on Great Britain Application Number 0309383.8, filed on Apr. 25, 2003, for priority.

U.S. patent application Ser. No. 12/712,476 is also a continuation-in-part application of U.S. patent application Ser. No. 12/364,067, entitled "X-Ray Sources" and filed on Feb. 2, 2009.

U.S. patent application Ser. No. 12/712,476 is also a continuation-in-part application of U.S. patent application Ser. No. 12/211,219, entitled "X-Ray Monitoring", filed on Sep. 16, 2008, and issued on May 25, 2010 as U.S. Pat. No. 7,724,868.

U.S. patent application Ser. No. 12/712,476 is also a continuation-in-part application of U.S. patent application Ser. No. 12/097,422, entitled "X-Ray Tomography Inspection Systems", filed on Jun. 13, 2008, and issued on Jan. 25, 2011 as U.S. Pat. No. 7,876,879.

U.S. patent application Ser. No. 12/712,476 is also a continuation-in-part application of U.S. patent application Ser. No. 10/554,570, entitled "X-Ray Scanning System", filed on Oct. 25, 2005, and issued on Mar. 23, 2010 as U.S. Pat. No. 7,684,538.

U.S. patent application Ser. No. 13/032,593 is also a continuation-in-part application of U.S. patent application Ser. No. 12/485,900, entitled "X-Ray Scanners and X-Ray Sources Therefor", filed on Jun. 16, 2009, and issued as U.S. Pat. No. 7,949,101 on May 24, 2011, which is a continuation-in-part application of U.S. patent application Ser. No. 12/097,422, entitled "X-Ray Tomography Inspection Systems", filed on Jun. 13, 2008, and issued on Jan. 25, 2011 as U.S. Pat. No. 7,876,879.

Each of the aforementioned PCT, foreign, and United States applications, and any applications related thereto, is herein incorporated by reference in their entirety.

FIELD OF THE INVENTION

The present invention relates to X-ray inspection systems. More particularly, the present invention relates to a source-detector configuration, whereby the energy transmitted through an object being inspected is measured at a wide range of substantially mono-energetic energies.

BACKGROUND OF THE INVENTION

Due to persistent security threats and the possibility of terrorist activities, there is a need for deploying high speed, high resolution, and more accurate screening devices at places that are most likely targets of such activities. In addition, there exists a requirement for screening of baggage, cargo and other items for explosives and other illicit materials. This requires a screening system which is capable of discriminating between different materials based on one or more unique features of each material such as effective atomic number, chemical structure, physical density, among other variables.

The use of X-ray computed tomography for the screening of baggage has become fairly common in recent times, since the cross-sectional image data that such imaging systems produce is generally of high quality and of reasonable quantitative accuracy. Known tomographic imaging systems tend to be based on a rotating gantry which carries, as a minimum, an X-ray source with a large stationary array of detectors and more commonly an X-ray source and an opposing array of X-ray detectors which rotate together around the object under inspection. The information collected is reconstructed using known algorithms, such as a filtered backprojection algorithm or an iterative algorithm to produce a two-dimensional image.

In more recent systems, the object is able to move continuously through the imaging plane during data acquisition and, through the use of a cone-shaped X-ray beam with a two dimensional array of detectors, a three-dimensional reconstructed image is produced using filtered back-projection or iterative reconstruction methods. In a further scanning embodiment, a stationary gantry system may be envisaged with a complete ring of rapidly switchable X-ray sources and a sensor array comprising one or more rings of X-ray detectors which may be used to form a three-dimensional image as the item under inspection passes through the imaging plane.

Such images, however produced, are capable of being reconstructed into an image that is substantially determined by the mass attenuation coefficient of the material under inspection. The mass attenuation coefficient is determined through the combination or probabilities of X-ray interaction in the object through the photoelectric effect (absorption), Compton effect (inelastic scattering), Rayleigh effect (elastic scattering) and the density of the material. The individual detector thus sees an intensity of radiation at any point in time which is due to both those primary X-rays which have passed through the object unimpeded (i.e. without being absorbed and without being scattered) and those which have arrived at the detector due to one or more scattering interactions.

The mass attenuation coefficient is equal to the linear attenuation coefficient divided by density. The linear attenuation coefficient is a quantity that characterizes how easily a material or medium can be penetrated by a beam of light, sound particles, or other energy or matter. A large attenuation coefficient means that the beam is quickly "attenuated" or weakened as is passes through the medium, and a small attenuation coefficient means that the medium is relatively transparent to the beam. Therefore, the atomic number of the material under inspection plays a dominant role in determining the effective linear attenuation coefficient through its impact on the probability of photoelectric effect interactions while the density of the material plays a significant role in determining the mass attenuation coefficient of the material.

Thus, there is a need for an improved X-ray inspection system and method that detects the presence of predefined materials based on the mass attenuation coefficients of the materials.

SUMMARY OF THE INVENTION

The present specification discloses a method for processing X-ray data to determine an identity of an object under inspection, comprising: transmitting a plurality of X-rays, wherein said X-rays have a range of energies, through the object; detecting said transmitted X-rays at a detector array, wherein each detector in said detector array outputs a signal proportional to an amount of energy deposited at said detector by a detected X-ray; reconstructing an image from said signal, wherein each pixel within the image represents an associated mass attenuation coefficient of the object under inspection at a specific point in space and for a specific energy level; fitting each of said pixels to a function to determine the mass attenuation coefficient of the object under inspection at the point in space; and using said function to determine the identity of the object under inspection.

Optionally, the function yields a relationship between mass attenuation coefficients and logarithmic values of energy. The function relates the energy response of the detector array at each energy within the range of energies multiplied by a function of the object's linear attenuation coefficient and density. Determining the identity of the object under inspection is performed by comparing the object's linear attenuation coefficient function to data comprising linear attenuation coefficient functions of predefined materials. The comparison yields a fit comparing the relationship between mass attenuation coefficients and logarithmic values of energy obtained from the object under inspection to pre-computed material data for known materials. Based on said comparison, pixels which are determined to qualify as potential threat materials are highlighted within said image. The energies are substantially mono-energetic energies. The mono-energetic energies are within a range of 20 keV to 250 keV.

The detectors output the signal proportional to the amount of energy deposited at said detector by the detected X-ray to an amplifier. The amplifier amplifies said signal and outputs said amplified signal to a multi-channel analyzer. The reconstruction is performed by processing said signal in accordance with at least one of a filtered back projection algorithm or an iterative reconstruction method. At least one image is reconstructed for each energy level detected by the detector array. The detector array has a resolution of 10 keV and wherein said energy source has a peak electron energy of at least 200 keV. A set of at least twenty images are reconstructed. Twenty images are derived from signals corresponding to X-rays having energies of at least 10 keV, 20 keV, 30 keV, 40 keV, 50 keV, 60 keV, 70 keV, 80 keV, 90 keV, 100 keV, 110 keV, 120 keV, 130 keV, 140 keV, 150 keV, 160 keV, 170 keV, 180 keV, 190 keV, and 200 keV. At least one image is reconstructed for each energy bin defined by the detector array. Energy bins are defined by 50 keV increments. Based on said energy bins, four images are reconstructed.

In another embodiment, the present specification discloses an X-ray system for processing X-ray data to determine an identity of an object under inspection, comprising: an X-ray source for transmitting a plurality of X-rays, wherein said X-rays have a range of energies, through the object; a detector array for detecting said transmitted X-rays, wherein each detector in said detector array outputs a signal proportional to an amount of energy deposited at said detector by a detected X-ray; and at least one processor having access to a memory for storing programmatic instructions, wherein when said programmatic instructions are executed, said processor: a) reconstructs an image from said signal, wherein each pixel within the image represents an associated mass attenuation coefficient of the object under inspection at a specific point in space and for a specific energy level; b) fits each of said pixels to a function to determine the mass attenuation coefficient of the object under inspection at the point in space; and c) uses said function to determine the identity of the object under inspection.

Optionally, the function yields a relationship between mass attenuation coefficients and logarithmic values of energy. The function relates the energy response of the detector array at each energy within the range of energies multiplied by a function of the object's linear attenuation coefficient and density. Determining the identity of the object under inspection is performed by comparing the object's linear attenuation coefficient function to data comprising linear attenuation coefficient functions of predefined materials. The comparison yields a fit comparing the relationship between mass attenuation coefficients and logarithmic values of energy obtained from the object under inspection to pre-computed material data for known materials. Based on said comparison, pixels which are determined to qualify as potential threat materials are highlighted within said image. The energies are substantially mono-energetic energies. The mono-energetic energies are within a range of 20 keV to 250 keV.

The X-ray system further comprises an amplifier for receiving and amplifying the signal proportional to the amount of energy deposited at said detector. The amplifier outputs said amplified signal to a multi-channel analyzer. At least one image is reconstructed for each energy bin defined by the detector array. The detector array has a resolution of 10 keV and wherein said energy source has a peak electron energy of at least 200 keV. A set of at least twenty images are reconstructed. Twenty images are derived from signals corresponding to X-rays having energies of at least 10 keV, 20 keV, 30 keV, 40 keV, 50 keV, 60 keV, 70 keV, 80 keV, 90 keV, 100 keV, 110 keV, 120 keV, 130 keV, 140 keV, 150 keV, 160 keV, 170 keV, 180 keV, 190 keV, and 200 keV. At least one image is reconstructed for each energy bin defined by the detector array. The energy bins are defined by 50 keV increments. Based on said energy bins, four images are reconstructed.

In another embodiment, the present specification discloses an X-ray system for processing X-ray data to determine an identity of an object under inspection, comprising an X-ray source for transmitting a plurality of X-rays, wherein said X-rays have a range of energies, through the object; and a detector array for detecting said transmitted X-rays, wherein said detector array comprises a first detector disposed in front of a second detector, and wherein said detector array is configured relative to the transmitted X-rays such that the transmitted X-rays pass through the first detector before passing through the second detector.

Optionally, the first detector is thinner than the second detector. The first detector has a scintillator thickness in a range of 0.2 mm to 1.0 mm. The second detector has a scintillator thickness in a range of 2.0 mm to 4.0 mm.

In another embodiment, the present specification discloses an X-ray system for processing X-ray data to determine an identity of an object under inspection, comprising an X-ray source for transmitting a plurality of X-rays, wherein said X-rays have a range of energies, through the object; and a detector array for detecting said transmitted X-rays, wherein said detector array comprises a first set of detectors and a second set of detectors, wherein each of said first set of detectors comprise scintillator material and a filter configured relative to the scintillator material such that the transmitted X-rays pass through the filter before passing through the scintillator material, and wherein each of said second set of detectors comprise scintillator material and do not comprise a filter.

Optionally, 25% to 50% of the detector array comprises the first set of detectors and wherein 75% to 50% of the detector array comprises the second set of detectors. The filter comprises copper with a thickness ranging from 0.2 to 0.5 mm. The first set of detectors detect a higher net energy X-ray spectrum than the second set of detectors. The first set of detectors and the second set of detectors are arranged in a tessellated pattern in the detector array. The first set of detectors and the second set of detectors are arranged in alternating rows in the detector array. Optionally, 1% to 4% of the detector array comprises the first set of detectors and wherein 99% to 96% of the detector array comprises the second set of detectors. Output signals from the first set of detectors are used to generate a first image and wherein output signals from said second set of detectors are used to generate a second image. The first image has a lower resolution than said second image. The first image has a higher energy than said second image. The first image and second image are used in combination to generate a dual energy analysis of said object.

These, and other embodiments, will described in further detail in the remainder of the specification.

BRIEF DESCRIPTION OF THE DRAWINGS

These and other features and advantages of the present invention will be appreciated, as they become better understood by reference to the following detailed description when considered in connection with the accompanying drawings, wherein.

DETAILED DESCRIPTION OF THE INVENTION

Figure 1:
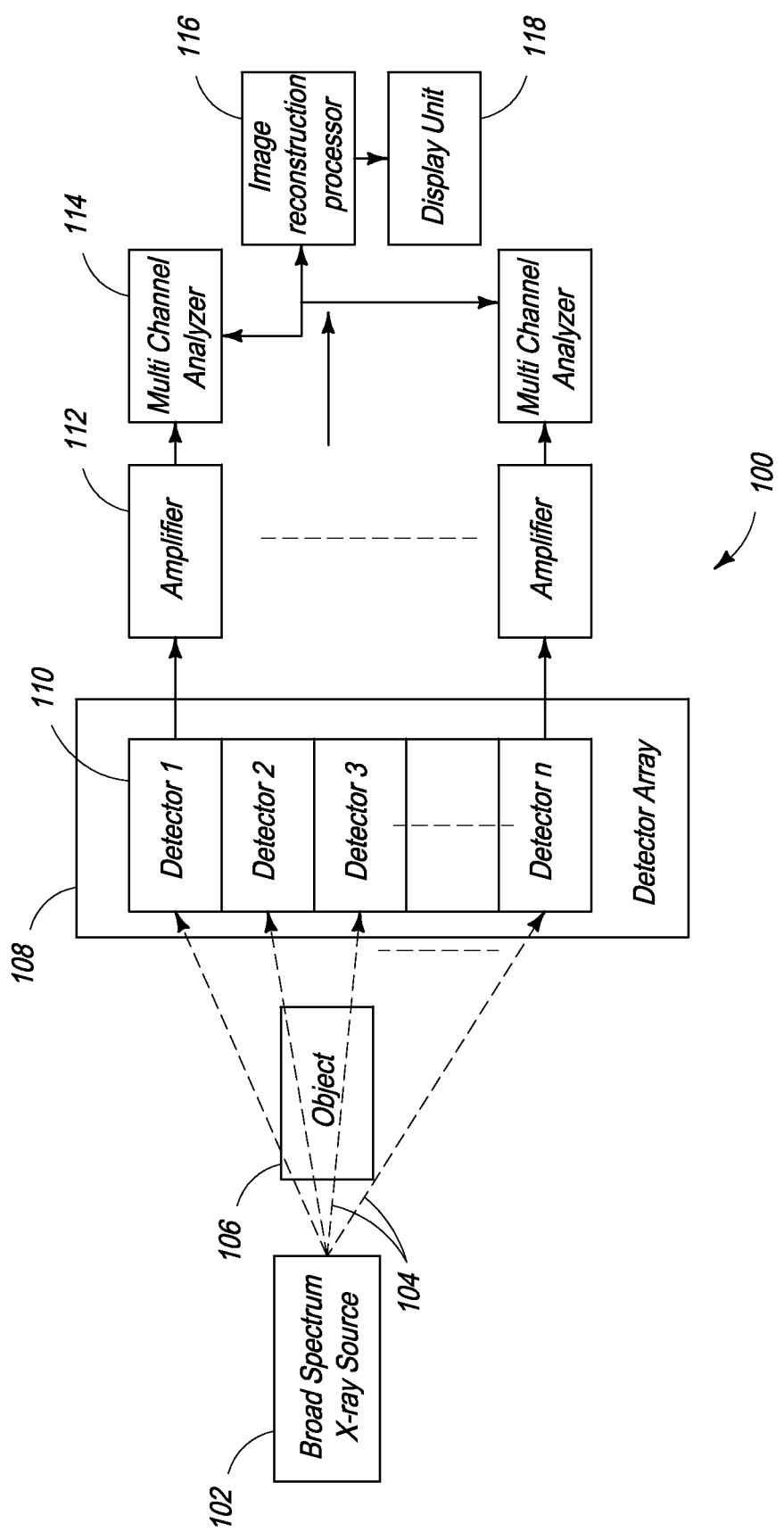
FIG. 1 illustrates an X-ray system, in accordance with one embodiment of the present invention.

The present invention relates to a source-detector configuration for use in an X-ray inspection system being used to inspect an object, whereby the energy transmitted through the object from the source to the detector is measured at a wide range of substantially mono-energetic energies. The measured energy is used to identify predefined threat material(s) in the object, if present.

X-ray sources that are typically used in screening of baggage, cargo and other similar items generally use a source that accelerates electrons in vacuum towards a target with a final kinetic energy at the target in the range of 50 keV to 200 keV depending on the intended application. Once these energetic electrons hit the target, they decelerate rapidly, liberating their energy though the Bremsstrahlung (scattering) effect or the photoelectric (absorption) effect which results in X-rays. The result is a Bremsstrahlung spectrum, a broad continuum of X-ray energies from the maximum accelerated electron energy down to zero, upon which a sharply peaked fluorescence spectrum is superimposed.

Since the linear attenuation coefficient varies rapidly with energy in the region below 500 keV, the wide range of energies that are contained within the X-ray beam can be used as a multi-energy probe of the linear attenuation coefficient of the material under inspection, thereby enabling a tight fit to the particular linear attenuation coefficient, and density, of the materials under inspection. In the present invention, it is recognized that the shape of the linear attenuation curve of a material is determined primarily by the atomic number of the material under inspection whereas the effective baseline of the curve is determined through the density of the material. For example, a gaseous material, such as Xenon, has a characteristic set of linear attenuation coefficients as a function of energy. When compressed from the gaseous state into a liquefied state, because of varying density of the states, the mass attenuation coefficient increases markedly, while the linear attenuation coefficient remains the same.

The present specification discloses multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

FIG. 1 illustrates an X-ray system in accordance with one embodiment of the present invention. The system 100 is used to inspect objects for identifying the presence of predefined threat material. The system 100 comprises an X-ray source 102 capable of emanating X-rays 104 having a broad energy spectrum, an object 106 requiring inspection, a detector array 108 comprising a plurality of detectors 110, a plurality of amplifiers 112, each of which is in data communication with at least one detector, a plurality of multi-channel analyzers 114, each of which is in data communication with at least one amplifier, an image reconstruction processor 116 in data communication with at least one multi-channel analyzer and a display unit 118 in data communication with the image reconstruction processor 116.

Figure 2:
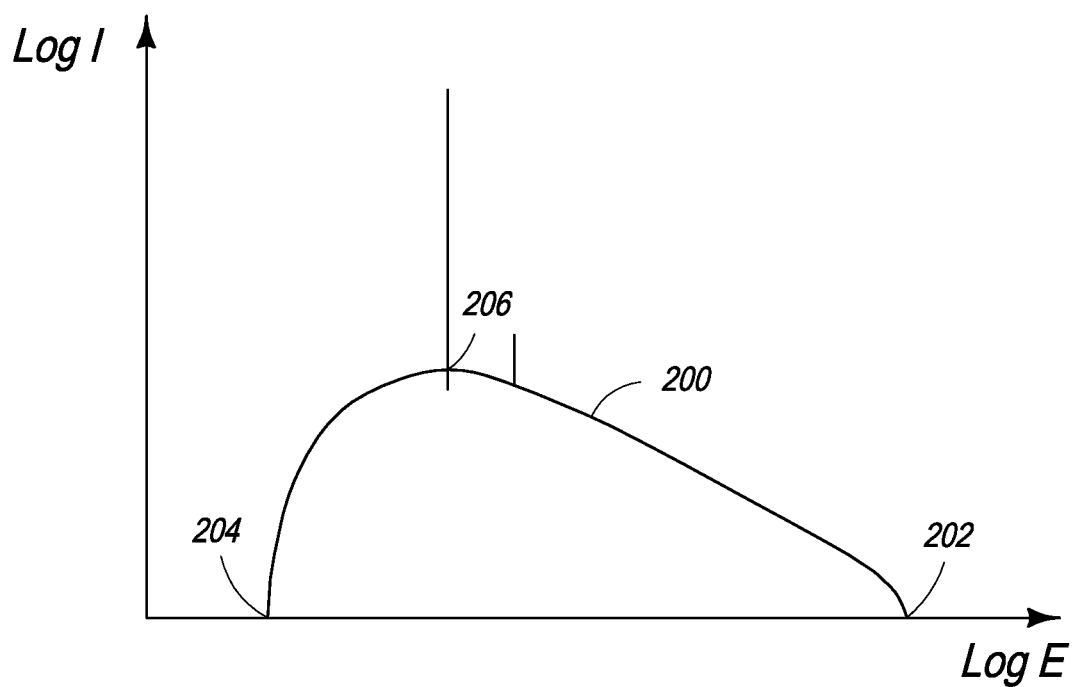
FIG. 2 illustrates the broad energy spectrum of an X-ray source, in accordance with one embodiment of the present invention.

FIG. 2 illustrates the energy spectrum of an X-ray source, in accordance with an embodiment of the present invention.

The curve 200 illustrated in FIG. 2 represents a typical Bremsstrahlung energy spectrum. The x-axis and the y-axis represent logarithmic values of energy and intensity, respectively. The spectrum comprises a slowly varying signal which trends toward zero 202 at higher energies and drops to zero 204 at low energies, and also displays one or more sharp peaks 206 at medium energies. The slowly varying signal is caused due to electron interactions in the target within an X-ray tube, and is known as Bremsstrahlung radiation.

The energy spectrum drops to zero 204 at low energies due to self-absorption of X-rays in the target and a vacuum window through which X-rays leave the X-ray tube. The peaked X-ray spectrum 206 is due to electron interactions in the target which result in fluorescence radiation. The spectrum peaks when all the energy of an electron which hits the target is converted to an X-ray. In various embodiments, the X-ray tubes as described in this disclosure tend to be operated with a tube voltage in the range 100 kVp to 200 kVp, and are capable of generating X-rays with energies up to 100 to 200 keV, respectively.

With reference to FIG. 1, the X-rays 104 emanating from the X-ray source 102 pass through the object 106 and the transmitted X-rays are detected by detectors 110 in the detector array 108. Each detector 110 in the detector array 108 is configured to, and capable of, outputting a signal that is proportional to the amount of energy deposited in the detector 110. In one embodiment, detector materials comprising narrow bandgap semiconductors such as Ge and Si are used in the detectors 110. In another embodiment, wider bandgap semiconductors such as CdZnTe, CdTe and HgI are used in the detector 110. In yet another embodiment, scintillation detectors with an opto-electronic readout such as, but not limited to, a NaI(T1) scintillator with a photomultiplier tube are used in the detector array 108.

Each detector 110 is in data communication with an amplifier 112, which, in turn, is in data communication with a multi-channel analyzer 114. The signal output by each detector 110 is amplified to a pre-defined degree by the amplifier 112 and transmitted to the multi-channel analyzer 114, which accumulates the transmitted X-ray spectrum for subsequent analysis and image reconstruction via image reconstruction processor 116. The reconstructed image is displayed via the display unit 118 which may be a computer screen. In an embodiment, the circuit illustrated in FIG. 1 is designed to detect the maximum output voltage from the amplifier 112 for each interacting X-ray and to convert this to a digital value. These digital values, one value per detected X-ray, are transmitted through a suitable digital interface to subsequent processing electronics such as the multi-channel analyzer 114. The electronics arrangement described above results in a detected X-ray spectrum of the form shown in FIG. 2, the shape of the detected spectrum being strongly affected by the type of material which is present between the X-ray source 102 and the X-ray detector 110.

As is known in the art, the energy required to liberate a signal carrier in a detector 110 varies with the type of detector material employed. In a semiconductor detector, this energy is typically below 5 eV, whereas in a scintillator detector, this energy is typically greater than 30 eV. For example, a 200 keV X-ray completely absorbed in a semiconductor detector with an efficiency of 2 eV per generated charge carrier, liberates 200/2=100 electrons. This corresponds to a charge of $1.6 \times 10^{-17}$ Coulombs.

In an embodiment, the amplifier 112 converts the liberated electrons to a voltage of 1V. Hence, a gain in the range of $1 \times 10^{14}$ to $1 \times 10^{17}$ V/C is required. In an embodiment, the amplifier 112 is designed to provide a linear response, so the voltage output by the amplifier 112 increases with an increase in the amount of energy deposited therein. Also, in an embodiment, a saturation point of the amplifier 112 is set such that it corresponds to an absorbed energy in the detector 110 which is greater than the maximum energy that can be generated by the combination of X-ray source 102 and detector 110. As would be evident to a person having ordinary skill in the art, a plurality of suitable amplifier 112 configurations such as, in one embodiment, an integrator with a reset switch which results in a step voltage output and integrator with resistive feedback which results in a smoothly varying pulsed output voltage, may be employed.

In various embodiments, at least one amplifier 112 and at least one multi-channel analyzer 114 is in data communication with each detector 110 in the detector array 108, resulting in a system with hundreds to thousands of individual energy sensitive detectors. The plurality of detectors 110 enable measurement of the energy spectrum transmitted through the object 106, rather than just the total energy deposited. Since, the energy spectrum is characteristic of the specific material of the object 106, measurement of the spectrum energy may be used to identify the presence of threat materials.

In various embodiments, a plurality of image reconstruction algorithms is used to analyze the accumulated X-ray spectrum for identifying the presence of predefined threat materials in the object 106. In an embodiment, the energy spectrum data from each of the multi-channel analyzers 114 is transmitted to an image reconstruction processor 116 in parallel for reconstructing a set of images by using one or more image reconstruction algorithms, each reconstructed image being characteristic of a particular energy in the detected spectrum.

Figure 3:
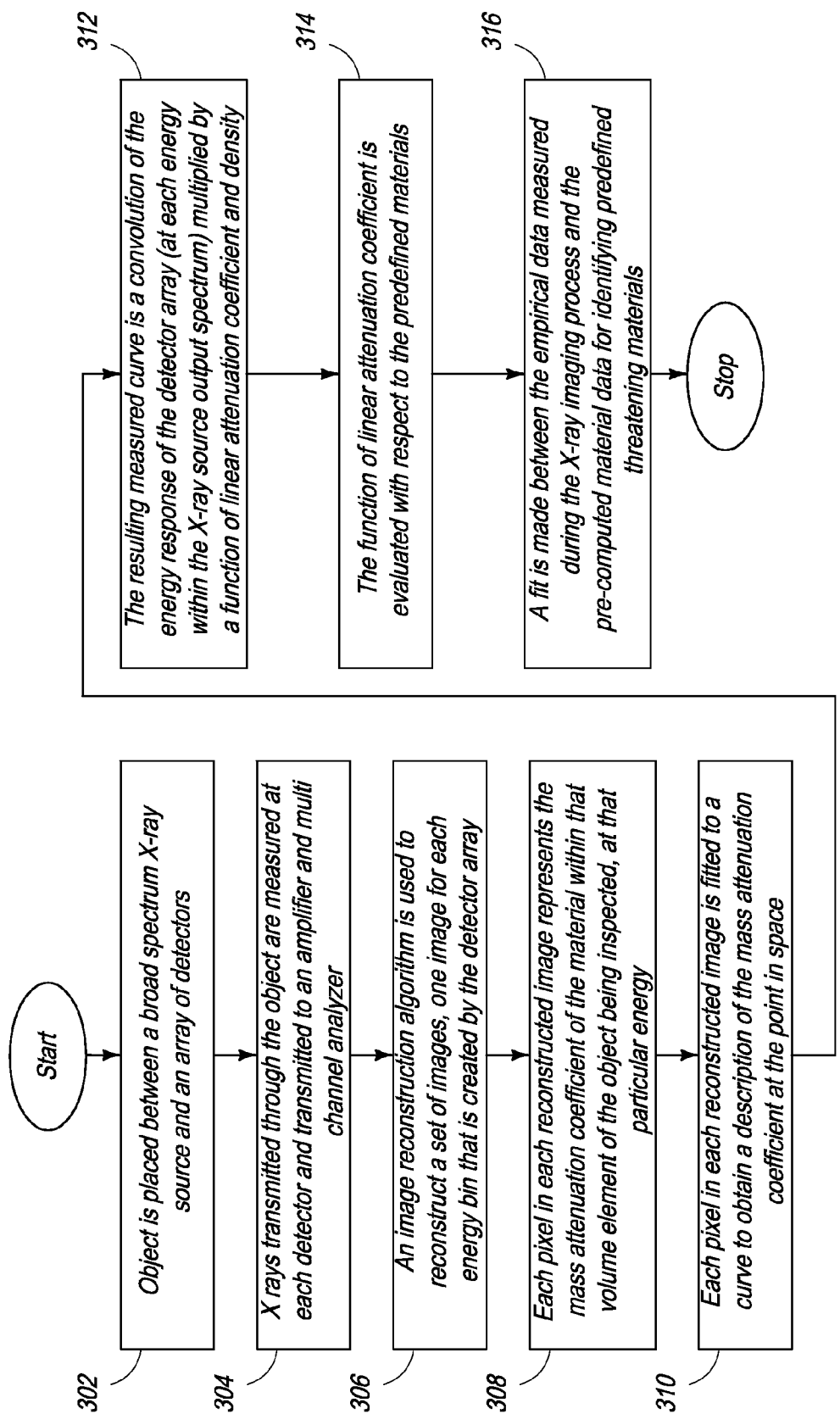
FIG. 3 is a flowchart illustrating a method for identifying predefined threat materials present in an object being inspected.

FIG. 3 is a flowchart illustrating a method for identifying materials present in an object being inspected using the system arrangement described above. At step 302, the object is placed between a broad spectrum X-ray source and an array of detectors. At step 304, X-rays transmitted through the object are measured at each detector. In various embodiments, the energy transmitted through the object from the X-ray source to the detector array is measured at a wide range of substantially mono-energetic energies. The range varies from the lowest energy generated (typically 20 keV and above), to the highest energy that is capable of being generated by the X-ray source (typically 250 keV and below).

The array of detectors comprises a plurality of detectors and each detector outputs a signal that is proportional to the amount of energy deposited in the detector by the impinging X rays, transmits to an amplifier and then to a multi-channel analyzer. At step 306, an image reconstruction algorithm is used to reconstruct a set of images, one image for each energy bin that is created by the detector array. In an embodiment, reconstructive algorithms like a filtered back projection algorithm and iterative reconstruction methods are used to reconstruct the set of images at step 306. For example, with a peak electron energy of 200 keV of the X-ray source, and a detector energy resolution of 10 keV, a set of 20 different images are reconstructed, at energies of 10 keV, 20 keV, 30 keV and so on up to 200 keV. In an exemplary scenario where typical energies are in the range 100 kVp to 250 kVp and the width of an energy bin is 10 keV to 50 keV a minimum of five images at 50 keV energy intervals and a maximum of 25 images at 10 keV intervals are generated. The underlying detector resolution lies in the range 1 keV (for a semiconductor detector) to 50 keV (for a typical scintillation detector). Thus, a system with 200 keV full scale with 10 keV energy bins would result in 20 reconstructed images whereas a system with 200 keV full scale and 50 keV bins would result in 4 reconstructed images.

At step 308, each pixel in each reconstructed image represents the mass attenuation coefficient of the material within that volume element of the object being inspected, at that particular energy. At step 310, each pixel in each reconstructed image is fitted to a curve to obtain a description of the mass attenuation coefficient at the point in space.

Figure 4:
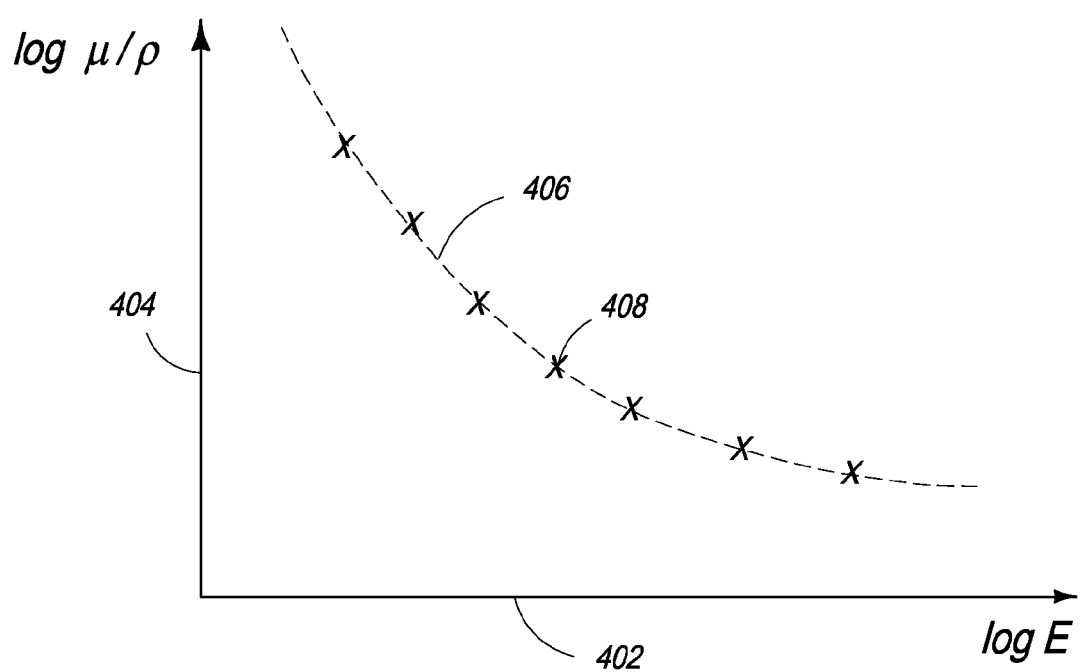
FIG. 4 illustrates the reconstructed image pixels fitted into a curve, in accordance with one embodiment of the present invention.

FIG. 4 illustrates the reconstructed image pixels fitted in a curve, in accordance with an embodiment of the present invention. The vertical axis 402 represents mass attenuation coefficient which may be represented as ($\mu/\rho$) (linear attenuation coefficient/density) whereas the horizontal axis 404 represents logarithmic values of Energy. The curve 406 illustrates the variation of mass attenuation coefficient as a function of X-ray energy. The measurement points 408 on the curve 406 indicate the reconstructed pixel values that are reconstructed for each of the energy bins.

Referring back to FIG. 3, at step 312, the resulting measured curve is a convolution of the energy response of the detector array (at each energy within the X-ray source output spectrum) multiplied by a function of linear attenuation coefficient and density. At step 314, the function of linear attenuation coefficient is evaluated with respect to a library of data defining linear attenuation coefficient functions of predefined materials. In an embodiment, the functions are evaluated experimentally. In another embodiment, the functions are calculated from known linear attenuation and density data for the materials. In either case, it should be appreciated that the known liner attenuation coefficient functions are stored in a data library which is stored, and accessed, either local to, or remote from, the system in a memory, such as a RAID array, hard disk, or any other form of memory.

At step 316, a fit is made between the empirical data measured during the X-ray imaging process (obtained at step 312) and the pre-computed material data for identifying threat materials. In an embodiment, the fit is made to determine the effective mass attenuation coefficient of a given material in the object under inspection. The mass attenuation coefficient is specific to each material in the pre-computed material data and is used to identify threat materials from benign materials. In an embodiment of the present invention, a least squares fitting method is used to provide a known statistical fit between sets of data to produce the most accurate analysis of material type. In an embodiment, the pixels which are determined to fall into the category of threat material are highlighted to an image inspector, for example through the use of color or image annotation. It should be appreciated that all of the image processing and data processing steps are performed by a processor executing on a plurality of programmatic instructions stored in a memory. The processor may be local to, or remote from, the X-ray source and detector array. The memory and programmatic instructions may be local to, or remote from, the X-ray source and detector array.

Figure 5:
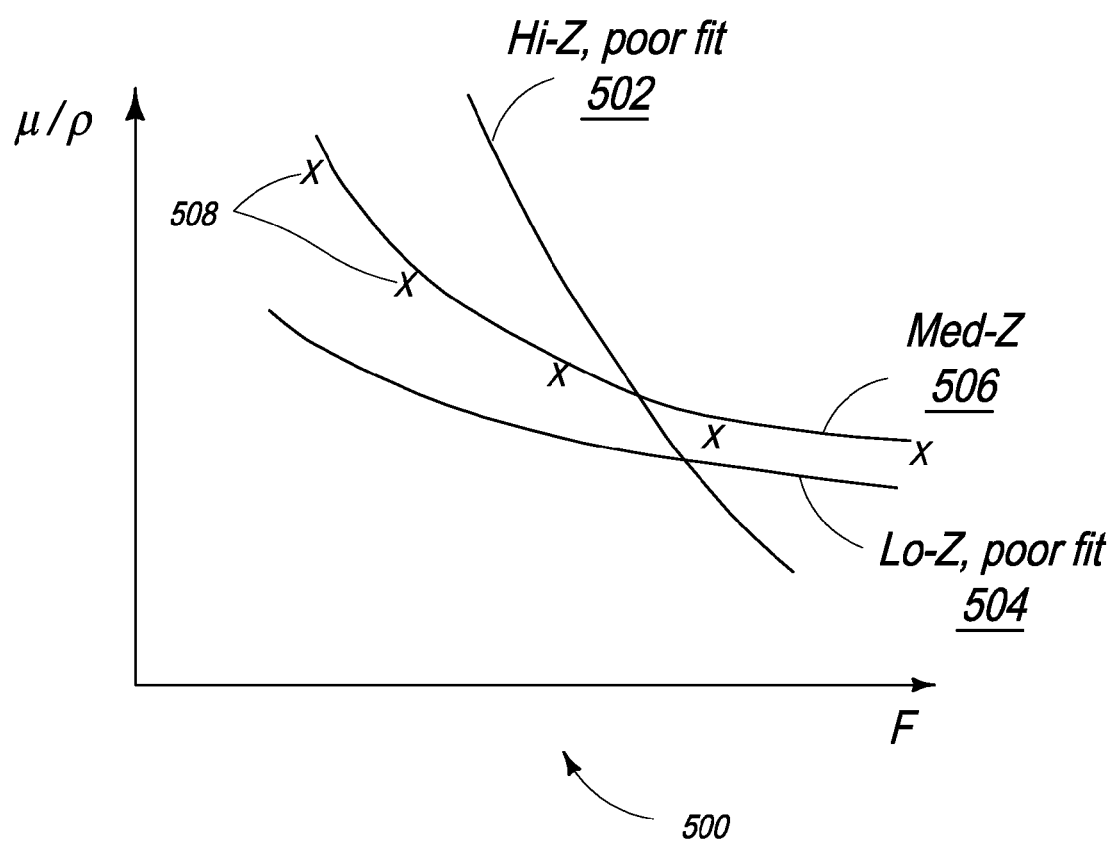
FIG. 5 is a graphical representation of the method for identifying predefined threat materials present in an object being inspected, in accordance with one embodiment of the present invention.

FIG. 5 is a graphical representation of the method for identifying predefined materials present in an object being inspected, in accordance with an embodiment of the present invention. The graph 500 represents a fitted curve between the empirical data measured during the X-ray imaging process and the pre-computed material data for identifying predefined materials as described with reference to FIG. 3.

The curve 502 represents the experimentally measured mass coefficient data with respect to a material having a high atomic number. The curve 504 represents the experimentally measured mass coefficient data with respect to a material having a low atomic number. Data generated from the empirical data measured during the X-ray imaging process is fitted to the curves 502, 504, and 506, as represented by data points 508.

Curves 502 and 504 represent a poor fit. The curve 506 represents the experimentally measured mass coefficient data with respect to a material having an atomic number lying between the high and the low atomic numbers corresponding to curves 502 and 504 respectively. The curve 506 demonstrates a good fit. Accordingly, in operation, the pixels corresponding to data points 508 would be deemed to correlate with, and potentially represent, medium atomic number materials. In the display unit, the pixels would be graphically highlighted as being medium atomic number materials, either by color, by intensity, or by any other visual means.

Figure 6A:
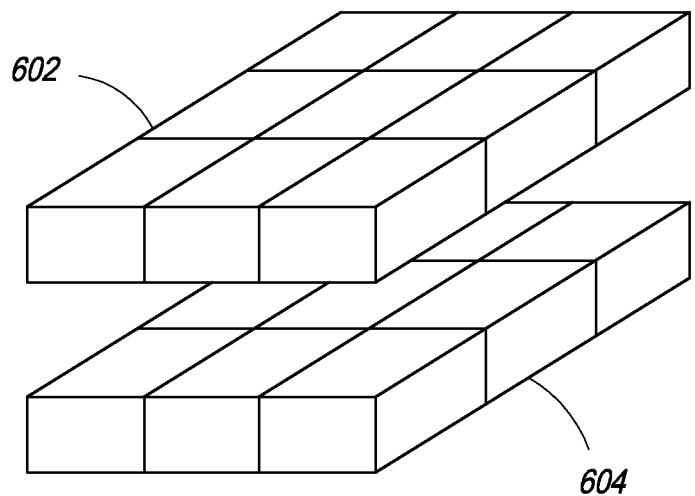
FIG. 6A illustrates a two-dimensional detector array configuration.

A plurality of detector array configurations that may be used in conjunction with the X-ray system illustrated in FIG. 1 are provided in FIGS. 6A, 6B, 6C, and 6D. FIG. 6A illustrates a two-dimensional detector array comprising a front detector 602 and a rear detector 604. Some X-rays pass through the front detector 602 to the rear detector 604, such that the rear detector 604 sees a higher average energy spectrum than the front detector 602. The front detector 602 is typically thin (0.2 mm to 1.0 mm scintillator material) compared to the rear detector 604 (typically 2.0 to 4.0 mm scintillator material).

Figure 6B:
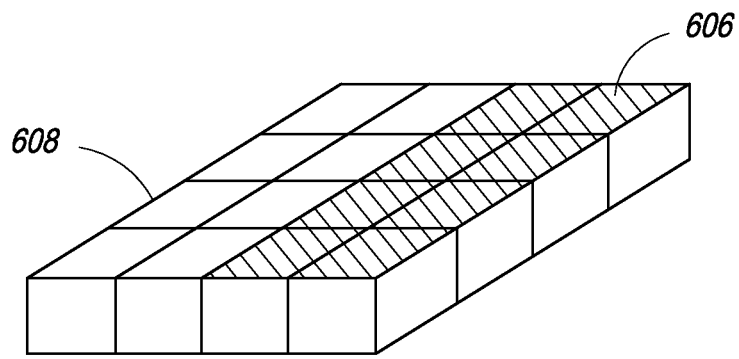
FIG. 6B illustrates a two-dimensional sensor array configuration.

FIG. 6B illustrates a two-dimensional sensor array in which a portion, such as a third or a half, of the rings 606 of a detector array are covered in a filter material while the other portion of the rings 608 are not. In most cases, the filter material is a metal, such as copper with a thickness ranging between 0.2 to 0.5 mm. The detectors 606 covered with the filter material experience a higher net energy X-ray spectrum than the uncovered detectors 608, and this difference is used to determine material type.

Figure 6C:
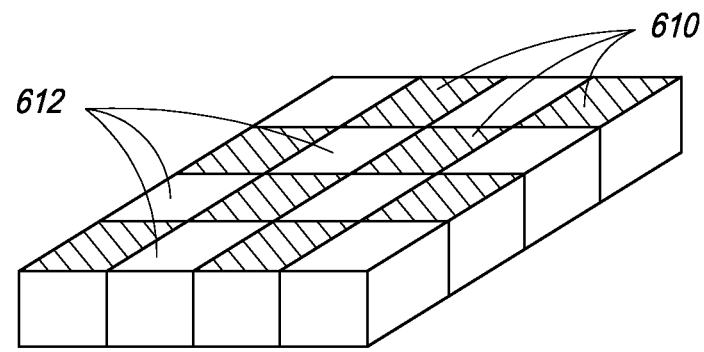
FIG. 6C illustrates an alternative filter configuration in a tessellated pattern.

FIG. 6C illustrates an alternative filter configuration in a tessellated pattern in which the filter material covers detectors 610 while detectors 612 remain uncovered. Hence, the filter material is spread at even intervals over the detector array.

Figure 6D:
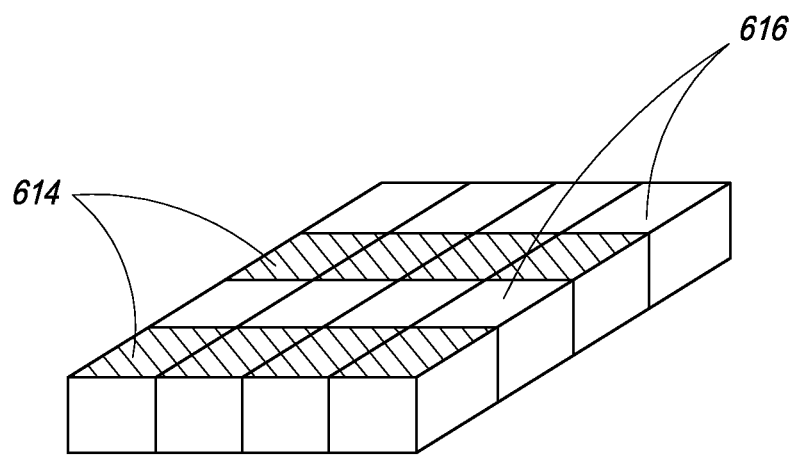
FIG. 6D illustrates a detector array structure where the filter material is applied on alternating rows of the detector.

FIG. 6D shows a detector array structure where the filter material is applied on alternating rows of the detector. Rows 614 are covered with a detector material while rows 616 remain uncovered.

In the detector array configurations illustrated in FIGS. 6A, 6B, 6C, and 6D, a large fraction of the imaging detector is dedicated to both filtered and non-filtered detectors, and this may compromise the quality of each of the reconstructed images produced by using the detector arrays in conjunction with the X-ray system illustrated in FIG. 1. It is preferred that the reconstructed image is of the highest quality in order to provide the best possible representation of the object under inspection. For example, a system with a stationary gantry may be configured with approximately 10,000 individual X-ray detectors and hundreds of individual X-ray source points resulting in a reconstructed image with a spatial resolution of approximately one millimeter and a mass attenuation coefficient resolution of better than one percent.

In order to provide material type through analysis of the shape of the mass attenuation coefficient curve, it is recognized that objects of interest tend to be large compared to the intrinsic pixel dimension and that the materials analysis data may be generated over a length scale which is long compared to the intrinsic image data. As an example, an improvised explosive device may contain a sizeable volume of explosive material, a detonating device, a trigger device, an energy source to supply the trigger and detonator devices, and/or some interconnecting wires. The intrinsic image resolution will ideally be able to provide good visualization of most, if not all, components of such a device, but the material type is only necessary to be estimated for the sizeable explosive component.

In various embodiments of the present invention, an image inspector processing unit is used to analyze intrinsically high resolution images having a high signal-to-noise ratio with a much lower resolution material type analysis that can be applied over larger contiguous volumes. As is known in the art, at an individual pixel level, there is a degree of noise which leads to uncertainty in the absolute value of detected mass attenuation coefficient, the uncertainty being described as signal-to-noise ratio. The signal-to-noise ratio is directly related back to the number of X-rays that interact in each detector. In order to improve signal-to-noise ratio, and hence the ability to discriminate between materials with similar mass attenuation coefficient, the signals are required to be averaged over a larger region. The system of the present invention enables analysis of data at multiple resolution levels, each with varying signal-to-noise ratio, in order to parameterize the measurement. Analysis at a high resolution level results in a higher degree of noise but better visualization of structure, whereas analysis at a low resolution level results in poor visualization of structure but leads to a closer identification of material type.

Figure 7:
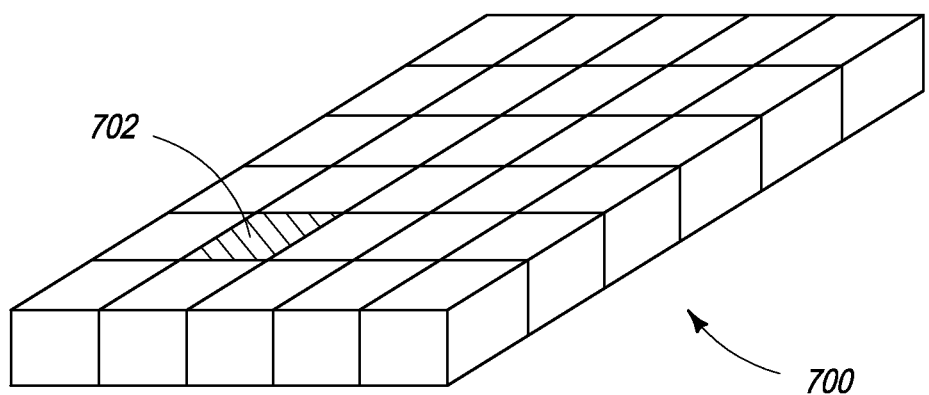
FIG. 7 illustrates a detector array configuration for producing high resolution images, in accordance with one embodiment of the present invention.

The present invention provides a detector array configuration for use in conjunction with the X-ray system illustrated in FIG. 1 to produce high resolution images. FIG. 7 illustrates a detector array configuration for producing high resolution images, in accordance with an embodiment of the present invention. The figure illustrates a multi-element pixel array 700. In an embodiment, the pixel array 700 is one commonly known in the art, such as those used in contemporary tomographic X-ray scanners. In an exemplary embodiment, the pixel array has 128 pixels arranged in a 16×8 pixel matrix. One of the pixels 702 of the pixel array 700 is covered with a filter material such as 0.2 mm to 1.0 mm of copper or aluminium. The effect of covering one pixel with the filter material has a minimal impact on the whole reconstructed image. In various embodiments, the exact numbers of filtered detectors depend on detailed system designs, but typically lie in the range of 1% to 4% of the total number of detector channels.

In an embodiment, a complete detector array comprises approximately 50 to 200 pixel arrays such as the one illustrated in FIG. 7, thereby providing over one hundred filtered pixel values that are more or less equally dispersed over the entire imaging volume. The values from just these sparsely located pixels may then be reconstructed using either a filtered backprojection or iterative reconstruction method to generate a low resolution but net high energy image which can then be fitted to the high resolution but lower average energy image to create materials specific data.

By placing a filter material over a small percentage of the detector array, i.e. from 1% to 4% of all detector elements, the system can generate a primary image which is reconstructed from the detector elements which are not filtered, i.e. 96% to 99% of all detector elements. The primary image is acquired by integrating over all X-ray energies, including the lowest X-ray energies, at a high spatial resolution. A secondary image, which has a lower resolution but higher mean X-ray energy, can also be generated using the filtered detector elements, i.e. 1% to 4% of the detector array. Once generated, the two images, namely the high resolution, lower energy primary image and lower resolution, higher energy secondary image, can be used in combination to generate, engage in, or otherwise conduct a dual energy materials analysis of materials under inspection.

While the exemplary embodiments of the present invention are described and illustrated herein, it will be appreciated that they are merely illustrative. It will be understood by those skilled in the art that various changes in form and detail may be made therein without departing from or offending the spirit and scope of the appended claims.

We claim:

1. An X-ray system for processing X-ray data to determine an identity of an object under inspection, comprising:
   an X-ray source for transmitting a plurality of X-rays, wherein said X-rays have a range of energies, through the object; and
   a detector array for detecting said transmitted X-rays, wherein said detector array comprises a first set of detectors and a second set of detectors, wherein each of said first set of detectors comprise scintillator material and a filter configured relative to the scintillator material such that the transmitted X-rays pass through the filter before passing through the scintillator material, wherein each of said second set of detectors comprise scintillator material and do not comprise a filter, and wherein 1% to 4% of the detector array comprises the first set of detectors and wherein 99% to 96% of the detector array comprises the second set of detectors.

2. The X-ray system of claim 1 wherein the filter comprises copper with a thickness ranging from 0.2 to 0.5 mm.

3. The X-ray system of claim 1 wherein the first set of detectors detect a higher net energy X-ray spectrum than the second set of detectors.

4. The X-ray system of claim 1 wherein the first set of detectors and the second set of detectors are arranged in a tessellated pattern in the detector array.

5. The X-ray system of claim 1 wherein the first set of detectors and the second set of detectors are arranged in alternating rows in the detector array.

6. The X-ray system of claim 1 wherein output signals from said first set of detectors are used to generate a first image and wherein output signals from said second set of detectors are used to generate a second image.

7. The X-ray system of claim 6 wherein the first image has a lower resolution than said second image.

8. The X-ray system of claim 7 wherein the first image has a higher energy than said second image.

9. The X-ray system of claim 8 wherein the first image and second image are used in combination to generate a dual energy analysis of said object.

* * * * *